United States Patent [19]
Osypka

[11] Patent Number: 5,738,683
[45] Date of Patent: Apr. 14, 1998

[54] MAPPING AND ABLATION CATHETER

[76] Inventor: Peter Osypka, Basler Strasse 109, D-79639 Grenzach-Wyhlen, Germany

[21] Appl. No.: 318,312

[22] Filed: Oct. 5, 1994

[30] Foreign Application Priority Data

Jul. 16, 1994 [DE] Germany ............. 44 25 195.5

[51] Int. Cl.$^6$ .................................. A61B 17/39
[52] U.S. Cl. .................. 606/47; 128/642; 607/122; 606/41; 606/39
[58] Field of Search ............... 606/32–34, 41, 606/42, 45–50; 128/642; 607/96–102, 115, 116, 119, 122, 123

[56] References Cited

U.S. PATENT DOCUMENTS

| | | | |
|---|---|---|---|
| 4,256,113 | 3/1981 | Chamness | 606/47 |
| 4,281,660 | 8/1981 | Fujiwara | 128/642 |
| 4,485,812 | 12/1984 | Harada et al. | 606/47 |
| 4,643,187 | 2/1987 | Okada | 606/47 |
| 4,699,147 | 10/1987 | Chilson et al. | 128/642 |
| 4,998,933 | 3/1991 | Eggers et al. | 606/31 |
| 5,024,617 | 6/1991 | Karpiel | 606/47 |
| 5,255,679 | 10/1993 | Imran . | |
| 5,263,493 | 11/1993 | Avitall | 128/642 |
| 5,279,299 | 1/1994 | Imran | 128/642 |
| 5,293,869 | 3/1994 | Edwards et al. | 128/642 |
| 5,318,564 | 6/1994 | Eggers | 606/47 |
| 5,327,889 | 7/1994 | Imran | 128/642 |
| 5,397,342 | 3/1995 | Heil, Jr. et al. | 128/642 |

FOREIGN PATENT DOCUMENTS

| | | |
|---|---|---|
| 0 609 182 A1 | 1/1994 | European Pat. Off. . |
| 40 25 369 A1 | 2/1991 | Germany . |
| 4122909 | 1/1993 | Germany . |
| 2 032 278 | 5/1980 | United Kingdom . |
| WO 95/15115 | 6/1995 | WIPO . |

*Primary Examiner*—Angela D. Sykes
*Assistant Examiner*—Michael Peffley

[57] ABSTRACT

A catheter which can be utilized for mapping and/or for ablation in the chamber or chambers of a heart or another body organ has a flexible sheath the distal end of which can be advanced through a blood vessel or another body passage into a selected chamber. A wire-like guide has a distal end portion affixed to the distal end of the sheath and is slidable in a lumen of the sheath so as to form a loop adjacent to and located externally of the distal end of the sheath. The guide and its loop are used as a device for steering the distal end portion of a tubular conductor assembly to any one of a number of different positions relative to the surface surrounding the chamber. The size of the loop is reduced prior to introduction of the distal end of the sheath into and prior to extraction of such distal end from a selected chamber. The catheter can be provided with a second guide serving to form a second loop at the distal end of the sheath and/or with one or more further guides having distal end portions slidable along the single loop or along one of plural loops. The distal end portion(s) of the further guide(s) can serve to steer the distal end portion(s) of one or more conductor assemblies along the surface bounding a selected chamber.

40 Claims, 9 Drawing Sheets

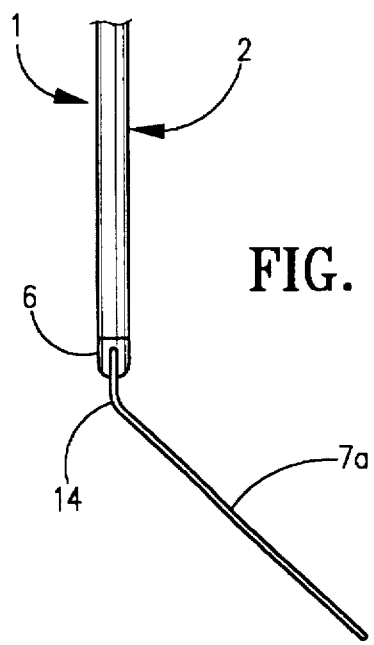
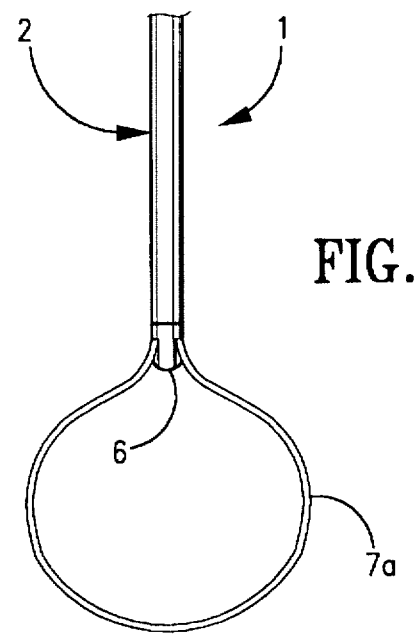
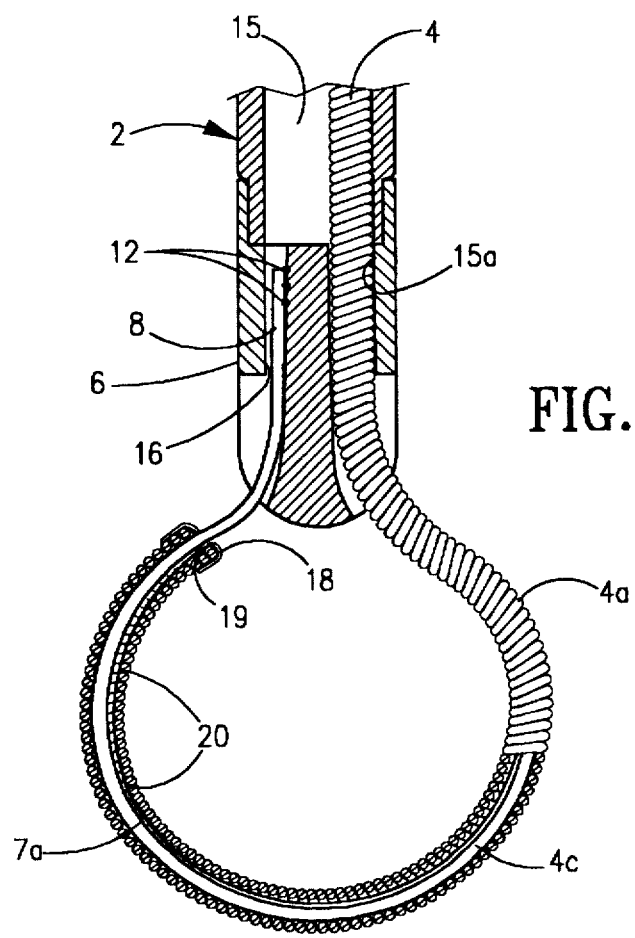

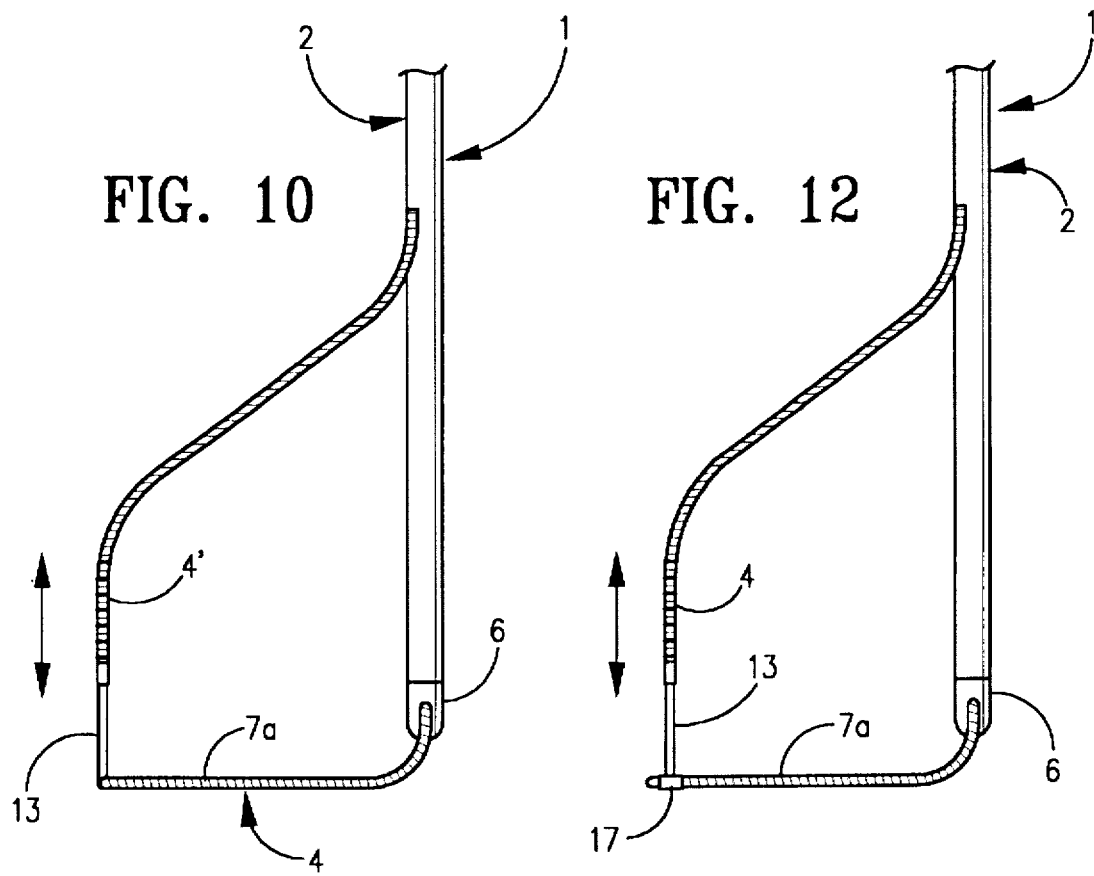
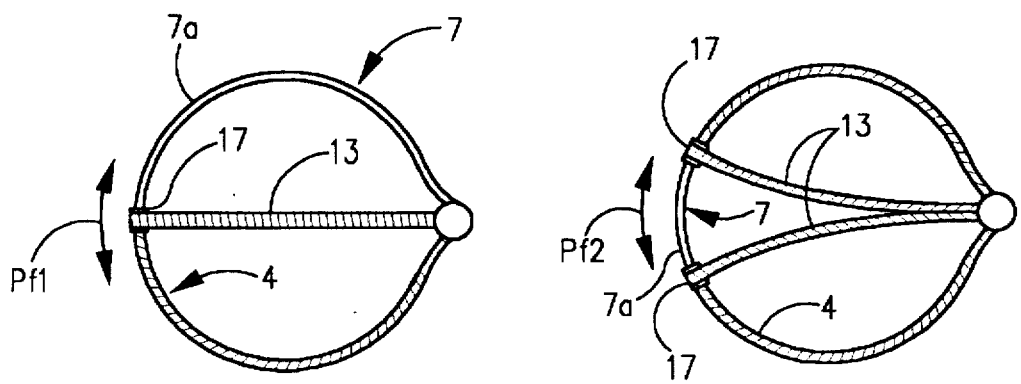

MAPPING AND ABLATION CATHETER

BACKGROUND OF THE INVENTION

The invention relates to catheters in general, and more particularly to improvements in so-called mapping or scanning catheters. Still more particularly, the invention relates to improvements in mapping catheters which can be utilized with advantage to scan selected parts of human hearts or other animal hearts.

It is known to detect cardiac signals and/or electric potentials with a catheter which employs a tubular envelope or sheath for confinement and longitudinal displacement of a composite conductor assembly including a set of discrete electrodes which are electrically insulated from each other and are provided with terminals or poles at the distal end of the conductor assembly. The sheath facilitates the introduction of the conductor assembly into a body organ, particularly into a heart, for the purpose of intracardial measurement and/or transmission of cardiac signals, for intracardial determination of electric potentials and/or for transmission of stimulating pulses.

The development of tachycardia is attributable to changes of networks and/or groups of cells. Presently known attempts to prevent the development of tachycardia (which is frequently lethal to a patient) include the destruction of the corresponding groups of cells. Such destruction can involve the application of heat by the application of high-frequency electrical energy and is known as high-frequency ablation. The application of high-frequency electrical energy for surgery other than within a heart is known for many years, e.g., for the purposes of coagulation.

The first step of treating a patient suffering from tachycardia is to accurately determine the locus and the cause of the affliction. This involves the utilization of a catheter of the aforedescribed character, i.e., a catheter employing a flexible sheath and a multiple electrode assembly whose distal end can be steered into a heart to carry out a mapping or scanning operation. The mapping constitutes an attempt to detect intracardiac signals which are indicative of the abnormal or degenerated cardiac network. The sheath of the catheter is introduced into the heart through a vein or through an artery so that its distal end is confined in a selected cardiac chamber. The detection or singling out of those networks and/or those groups of cells which cause the development of tachycardia by resorting to heretofore known catheters is a time-consuming procedure. Thus, it is necessary to map or scan the interior of the heart with the plural electrodes of the multiple electrode or conductor assembly. Problems arise in connection with the attempted scanning or mapping of hard-to-reach regions in a patient's heart and/or in connection with the attempted mapping or scanning of regions adjacent a smooth internal surface. Typical examples of heart portions which cannot be readily mapped because they are provided with smooth surfaces are cardiac valves as well as regions which are adjacent such valves. The reason is that it is difficult to adequately anchor the tips of electrodes in such a way that the electrodes can properly detect and transmit cardiac signals for interpretation by the heart specialists. Any mapping or scanning operation with catheters of the above outlined character must be carried out by highly skilled specialists and even such persons must exhibit much patience and must spend much time in order to complete the mapping operation prior to proceeding with ablation or other remedial procedures.

OBJECTS OF THE INVENTION

An object of the invention is to provide a novel and improved catheter which can be utilized for intracardial mapping or scanning and is constructed and assembled in such a way that it can reliably map any desired part of a heart regardless of the smoothness or coarseness of the surface or surfaces adjacent the regions or parts to be scanned.

Another object of the invention is to provide a novel and improved system of means for guiding and confining a multiple conductor assembly for introduction into a body cavity, such as a selected chamber of a human or other animal heart.

A further object of the invention is to provide a catheter which can complete a mapping or scanning operation within a heart or another body organ within a fraction of time necessary to carry out such operation with heretofore known catheters.

An additional object of the invention is to provide a catheter which can be utilized to properly and reliably position the poles or terminals of plural conductors within a body organ regardless of the characteristics of the adjacent internal surface of the organ.

Still another object of the invention is to provide a novel and improved combination of plural electrical conductors and guide means therefor for use in the above outlined catheter.

A further object of the invention is to provide the catheter with novel and improved means for reliably locating the terminals or poles of plural electrical conductors within a body cavity, for example, in a selected chamber of a human or other animal heart.

Another object of the invention is to provide a novel and improved catheter for the mapping of heart valves and of regions adjacent such valves.

An additional object of the invention is to provide a versatile catheter which can be rapidly converted to carry out any one of a variety of different mapping or scanning operations.

Still another object of the invention is to provide a catheter which can be utilized to carry out the aforeoutlined mapping or scanning operations as well as for ablation of tissue to be removed from a defective body organ.

A further object of the invention is to provide a novel and improved method of mapping selected areas of body organs.

Another object of the invention is to provide a catheter which can be used for reliable and speedy mapping of selected body organs without necessitating any anchoring of its electrodes in the monitored body organ.

An additional object of the invention is to provide a novel and improved catheter for the mapping of valves in human or other animal hearts.

Still another object of the invention is to provide a novel and improved flexible sheath for one or more groups of conductors which can be utilized in the above outlined catheter.

A further object of the invention is to provide a novel and improved combined mapping and ablation catheter for detection and elimination of causes of tachycardia.

Another object of the invention is to provide a catheter which, in addition to mapping and/or ablating, can also perform the function of stimulating a patient's heart.

An additional object of the invention is to provide a catheter which can be utilized to accurately and reliably position the poles or terminals of one or more sets of conductors relative to smooth internal surfaces of body organs without destroying the tissue of the organs.

Still another object of the invention is to provide a catheter which can be utilized for accurate and rapid mapping or scanning of each and every chamber in a human heart or another animal heart.

A further object of the invention is to provide a catheter which can be utilized for accurate, predictable and reliable positioning of the poles or terminals of one or more groups of electrical conductors relative to selected portions in the interior of body organs for the purposes of mapping or scanning, for the purposes of ablation and/or for the purposes of stimulation.

Another object of the invention is to provide a novel and improved combination of flexible sheath and one or more guides for sets or groups of conductors which can be utilized in the above outlined catheter.

SUMMARY OF THE INVENTION

The invention is embodied in a catheter which can be utilized as a mapping catheter or an ablation catheter and comprises an elongated flexible sheath which can be made of a suitable plastic material and has a distal end, an accessible proximal end and at least one lumen between the two ends. The catheter further comprises at least one elongated flexible guide having a looped portion at the distal end of the sheath and a strand disposed in the at least one lumen and movable longitudinally of the sheath to thereby change the size of the looped portion (namely the size of that part of the looped portion which is disposed externally of the sheath and is adjacent the distal end of the sheath), and conductor means having a distal end portion with one or more terminals or poles and being movable longitudinally of the strand to advance its distal end portion toward and along the looped portion of the at least one guide.

The conductor means can comprise two or more discrete conductors each of which has a terminal or a pole at the distal end portion of the conductor means. The conductors form part of a tube having a lumen for the at least one guide.

The improved catheter can further comprise a second elongated flexible guide having a distal end portion which is movable along the looped portion of the at least one guide and an elongated strand which is at least partially confined in and is movable relative to the sheath to thereby move the looped portion relative to the distal end of the sheath and/or to move the distal end portion of the second guide relative to and along the looped portion of the at least one guide. The lumen of the aforementioned tube which is formed by the discrete conductors of the conductor means can receive the strand of the at least one guide or the strand of the second guide preparatory to moving the distal end portion of the conductor means toward or away from the distal end portion of the second guide or toward and along the looped portion of the at least one guide.

The improved catheter can further comprise second conductor means which may but need not be identical with the first mentioned conductor means and also comprises a distal end portion with one or more terminals or poles. The second conductor means can be moved longitudinally of the strand of the second guide to thus move the distal end portion of the second conductor means toward or away from the distal end portion of the second guide. Furthermore, the catheter is preferably constructed and can be assembled in such a way that the distal end portion of the second conductor means is also movable along the looped portion of the at least one guide jointly with the distal end portion of the second guide.

The distal end portion of the second guide is preferably movable between an infinite number of different positions relative to the distal end of the sheath as well as along the looped portion of the at least one guide. Furthermore, the strand of the at least one guide is preferably movable relative to the sheath between an infinite number of different positions to thus infinitely vary the size of the looped portion of the at least one guide.

The first mentioned and/or the second conductor means can comprise a plurality of (e.g., eight or ten) discrete helically convoluted conductors which are insulated from each other and form part of a tube defining a lumen for the at least one guide or for the second guide. Each of the plurality of discrete conductors can have an exposed terminal or pole at the distal end portion of the respective conductor means. The at least one guide and/or the second guide can constitute a length of suitably shaped metallic or plastic wire, and the diameter of such wire at most matches the diameter of the lumen in the first mentioned and/or in the second conductor means. This ensures that the tube is readily slidable along and around the at least one guide and/or along and around the second guide.

The at least one guide can be configurated and mounted in such a way that a first end of the looped portion is anchored in the distal end of the sheath and that a second end of the looped portion merges into the strand of the at least one guide. The strand of the at least one guide has a proximal end at the proximal end of the sheath and the distal end portion of the first mentioned or the second conductor means is movable along and beyond the proximal end of the strand forming part of the at least one guide all the way toward and along the looped portion and preferably all the way or at least close to the first end of the looped portion.

The first end of the looped portion can be affixed to the distal end of the sheath in any one of a number of different ways, e.g., by anchoring it in a socket provided therefor in the distal end of the sheath. The at least one guide preferably includes a resiliently deformable section or portion which is disposed at and tends to maintain the looped portion in a plane making an obtuse angle with the distal end of the sheath. Such resiliently deformable section can be adjacent the first end of the looped portion.

The at least one lumen of the sheath has an outlet which is or which can be disposed diametrically opposite the first end of the looped portion, i.e., substantially diametrically opposite that part of the looped portion which is anchored in the distal end of the sheath. The second end of the looped portion (namely the end which merges into the strand of the at least one guide) is movable by the strand of the at least one guide relative to the sheath (i.e., relative to the outlet of the at least one lumen) to thus withdraw a selected part of the looped portion into the at least one lumen or to increase that part of the looped portion which is located outside of the distal end of the sheath.

As mentioned above, the at least one guide can include a section which maintains the looped portion of the at least one guide in a predetermined plane until and unless the looped portion is subjected to deforming stresses (e.g., by moving along an internal surface of a human heart). If such catheter is further provided with the aforementioned second guide, the distal end portion of the second guide engages the looped portion of the at least one guide and the strand of the second guide is at least partially confined in and is movable longitudinally of the sheath to position the distal end portion of the second guide in such a way that it is inclined relative to the plane of the looped portion of the at least one guide. The distal end portion of the second guide can be provided with a follower (e.g., a hook or an eyelet) which is movable along the looped portion of the at least one guide. The sheath which forms part of such catheter can be provided with a second outlet through which the strand of the second guide can move from the at least lumen of the sheath to the exterior of the sheath or in the opposite direction. The second outlet is preferably spaced apart from the distal end of the sheath, i.e., from that outlet of the at least one lumen through which the strand of the at least one guide extends and which is or which can be located substantially diametrically opposite the first end of the looped portion.

The follower of the distal end portion of the second guide can be moved along the looped portion of the at least one guide by the first mentioned conductor means, by the second conductor means or by moving means provided for the express purpose of moving the follower along the looped portion of the at least one guide. If the follower is to be moved by one of the conductor means, the distal end portion of such conductor means is caused to advance along the strand and thereupon around and beyond the second end of the looped portion of the at least one guide to advance the follower (e.g., stepwise) in a direction from the second toward the first end of the looped portion of the at least one guide. The moving means can comprise an elongated flexible tubular member having a lumen which can slidably receive the strand of the at least one guide and a distal end portion which is movable along the looped portion of the at least one guide to thereby move the follower relative to the looped portion of the at least one guide.

If the improved catheter employs the at least one conductor and the second conductor, the first mentioned conductor means can be used to move its distal end portion along the strand toward and along the looped portion of the at least one guide, and the second conductor means can be used to move its distal end portion along the strand and along the distal end portion of the second guide. The second conductor means can include or constitute a tube having a lumen with a diameter which at least equals but can exceed the diameter of the second guide (e.g., a length of metallic or plastic wire). The tube can include a plurality of helically convoluted discrete conductors which are insulated from each other and include terminals or poles at the distal end portion of the second conductor means. It is also possible to provide a tube which includes a single helically convoluted or otherwise shaped electrical conductor.

The proximal end of the first mentioned conductor means and/or the proximal end of the second conductor means can be connected to a suitable source of high-frequency energy. The proximal end of the first mentioned conductor means and/or the proximal end of the second conductor means can be disposed at least close to the proximal end of the sheath. The distal end portion of the first mentioned and/or the second conductor means can carry a temperature sensor. Such sensor can be positioned adjacent the terminal or terminals at the distal end portion of the first mentioned or the second conductor means. A catheter with one or more conductor means connectable to a source of high-frequency energy can be combined with or can comprise means for regulating the transmission of high-frequency energy from the source to at least one terminal at the distal end portion of the first mentioned and/or second conductor means in response to signals from the temperature sensor.

Each guide is preferably made of an elastically deformable material which can be a metallic material or a plastic material.

The improved catheter can be furnished with an additional guide which can but need not be identical with the at least one guide. Such additional guide also comprises a looped portion at the distal end of the sheath and a strand which is disposed in and is movable longitudinally of the sheath to vary the size of the looped portion of the additional guide. The two looped portions are preferably located in different planes which are outwardly adjacent the distal end of the sheath. The strands of the at least one guide and of the additional guide can be confined in the at least one lumen of the sheath, and the outlet of the at least one lumen for the sheaths of the at least one guide and the additional guide can be provided at (e.g., directly in) the distal end of the sheath. The looped portions of the at least one guide and of the additional guide are located outside of the sheath and at the distal end of the sheath. One of the planes for the two looped portions makes with the distal end of the sheath a first angle and the other plane makes with such distal end a larger second angle. If such catheter employs the aforementioned second guide, the distal end portion of the second guide engages that looped portion which is located in the one plane. The follower of the distal end portion of the second guide is preferably movable along the looped portion in the one plane.

The catheter can be constructed and assembled in such a way that it includes the at least one guide, the second guide and a further guide which can but need not be identical with the second guide. The distal end portions of the second guide and the further guide engage the looped portion of the at least one guide and the strands of the second guide and the further guide are at least partially confined in the sheath. The distal end portion of the second guide and/or the distal end portion of the additional guide can include a follower which is slidable along the looped portion of the at least one guide.

If the catheter comprises the at least one guide, the additional guide and the second guide, it can further comprise the aforementioned further guide. The distal end portion of the second guide preferably engages the looped portion of the at least one guide and the distal end portion of the further guide can engage the looped portion of the additional guide.

It is further possible to construct and assemble the catheter in such a way that it comprises the at least one guide, the second guide and the further guide. The distal end portions of the second guide and of the further guide engage the looped portions of the at least one guide, and the distal end portions of the second guide and the further guide can be spaced apart from each other.

Still further, the catheter can be constructed and assembled in such a way that it comprises the at least one guide, a hollow tubular guide having a distal end portion at the looped portion of the at least one guide and a second portion which is at least partially confined in the sheath, and further conductor means confined in the tubular guide and including a distal end portion which is movable beyond the distal end portion of the tubular guide. The distal end portion of the further conductor means can be substantially J-shaped. Such catheter can be used for mapping a heart, e.g., by moving the looped portion of the at least one guide toward and against one side of a heart valve and by moving the J-shaped distal end portion of the further conductor means through the valve and toward the other side of such valve.

The novel features which are considered as characteristic of the invention are set forth in particular in the appended claims. The improved catheter itself, however, both as to its construction and the mode of assembling and utilizing the same, together with additional features and advantages thereof, will be best understood upon perusal of the following detailed description of certain presently preferred specific embodiments with reference to the accompanying drawings.

BRIEF DESCRIPTION OF THE DRAWINGS

FIG. 2 is a side elevational view of that portion of the catheter which is shown in FIG. 1 but prior to insertion into or subsequent to extraction from the heart chamber;

FIG. 3 is a view of the catheter portion as seen in a direction from the right or from the left of FIG. 2;

FIG. 4 is an enlarged central longitudinal sectional view of the sheath of the catheter of FIGS. 1 to 3, an elevational view of the looped portion of the flexible guide, and a partly elevational and partly sectional view of tubular conductor means having a lumen for the strand and for the looped portion of the flexible guide;

FIG. 10 is a fragmentary elevational view of the catheter of FIG. 6 and further shows a second conductor assembly which is used to shift the follower of the distal end portion of the second guide along the looped portion of the first guide;

FIG. 11 is a bottom plan view of the structure shown in FIG. 10;

FIG. 12 is a view similar to that of FIG. 10 but showing an additional guide which has a follower engaging the looped portion of the first guide;

FIG. 13 is a bottom plan view of the structure which is shown in FIG. 12; and

DESCRIPTION OF PREFERRED EMBODIMENTS

Figure 1:
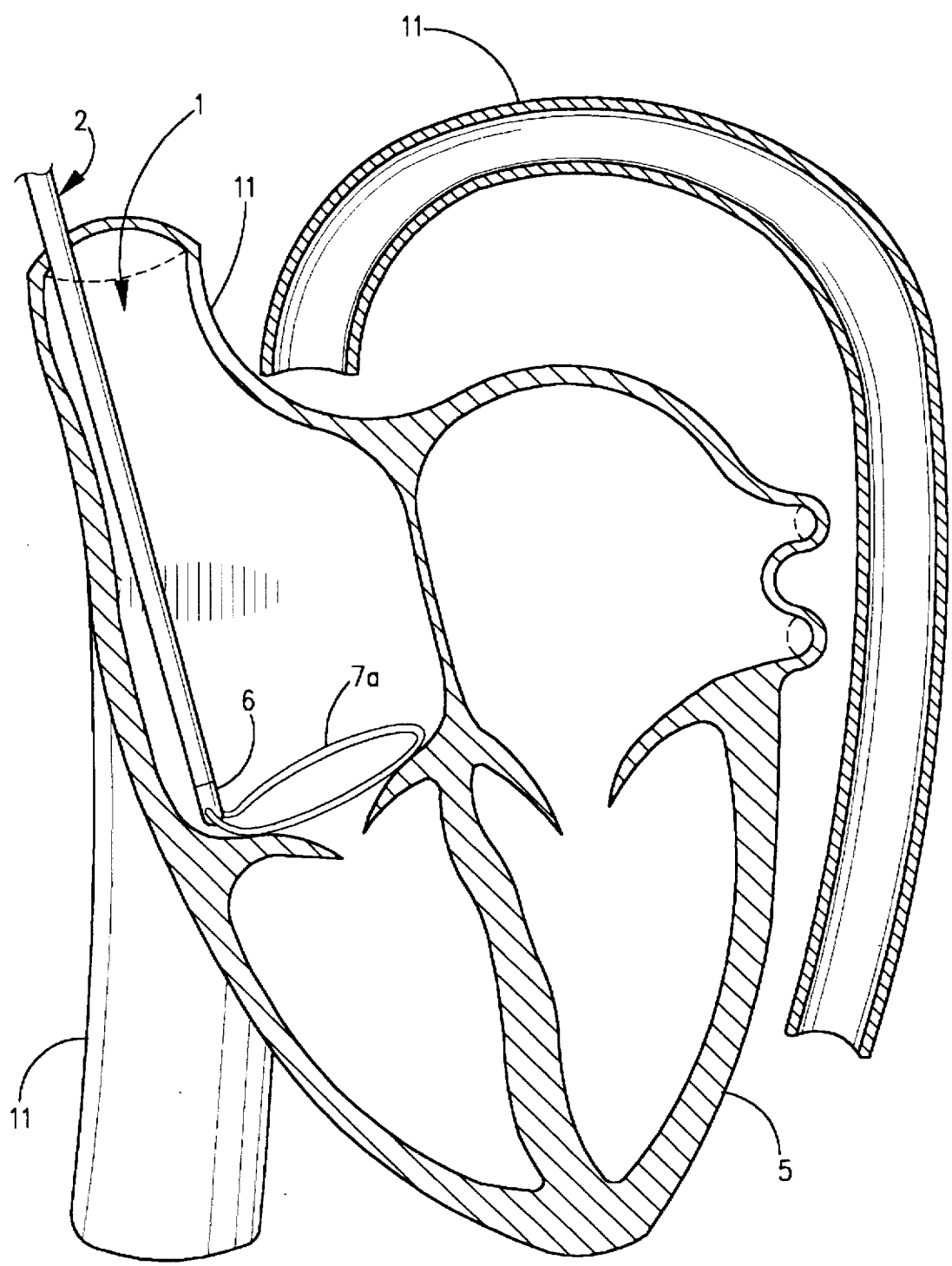
FIG. 1 is schematic sectional view of a heart and a fragmentary elevational view of a catheter which embodies one form of the present invention and comprises a single flexible guide having a looped portion positioned in one chamber of the heart adjacent one side of a heart valve.

Referring first to FIGS. 1 to 5, there is shown a catheter 1 which comprises an elongated flexible sheath 2 having a distal end 6, a proximal end 2a and an elongated lumen 15 extending between the two ends 2a and 6. The catheter further comprises an elongated flexible guide 7 having a looped portion 7a (hereinafter called loop for short) at its distal end, an elongated strand 9 in the lumen 15 and a proximal end provided with a handgrip portion 10 and extending outwardly beyond the proximal end 2a of the sheath 2. The loop 7a is outwardly adjacent the distal end 6 of the sheath 2 and includes a first end 8 anchored (at 12) in a socket 16 provided therefor in the distal end 6 of the sheath 2, and a second end which merges into the distal end of the strand 9. The handgrip portion 10 for the proximal end of the guide 7 can be manipulated relative to the handgrip portion 2d on the proximal end 2a of the sheath 2 in order to move the strand relative to the lumen 15 and to thus increase or reduce the size of the loop 7a. The catheter 1 of FIGS. 1 to 5 further comprises a conductor assembly or conductor means 4 having a distal end portion 4a and a proximal end portion 4b carrying a handgrip portion 4d which can be manipulated to cause the assembly 4 to slide around and along the guide 7 in a direction to move the distal end portion 4a toward and along the loop 7a (e.g., all the way or at least close to the first end 8 of the loop 7a) or in the opposite direction. The conductor assembly 4 comprises a tube formed by a set of, for example, six or more discrete electrical conductors 3 which are convoluted to form helices surrounding the guide 7 a portion of which is received in the lumen 4c of the tube forming part of the assembly 4. The diameter of the lumen 4c at least equals and can somewhat exceed the diameter of the metallic or plastic wire which is used to make the guide 7.

FIG. 4 shows that the lumen 15 of the sheath 2 has an outlet 15a in the distal end 6 and that the diameter of the outlet 15a suffices to ensure that the assembly 4 can be caused to move its distal end portion 4a through such outlet on its way toward or away from the first end 8 of the loop 7a. The helices of conductors 3 forming part of the assembly 4 are insulated from each other all the way from the proximal end portion 4b to the distal end portion 4a but the distal end portions of the conductors 3 are bare at selected locations of the distal end portion 4a to constitute terminals or poles (such as 18 or 20) which can be used to map selected portions of a heart 5, e.g., to map or scan one side of a valve between two chambers of the heart which is shown schematically in FIG. 1 of the drawings.

The poles or terminals 20 can be formed by removing insulation from the conductors 3 at the distal end portion 4a of the assembly 4. Such terminals remain insulated from each other but can be caused to contact selected portions in the interior of the heart 5 or in another body organ. The insulation is removed from relatively small (such as punctate or punctiform) portions of the conductors 3. The conductor assembly 4 can be utilized for point-by-point mapping or scanning of the internal surface of the heart 5 and/or for transmission of cardiac signals and/or for determination of electrical potentials in a patient's heart. Furthermore, and as will be described in detail hereinafter, the catheter 1 can be used with equal or similar advantage for cardiac surgery, e.g., to ablate selected parts of afflicted tissue. Still further, the catheter 1 can be utilized as an instrument which applies to the heart suitable stimulating impulses. FIG. 1 shows that the distal end 6 of the sheath 2 has been introduced into a cardiac chamber through the most convenient blood vessel 11 so that the exposed loop 7a of the guide 7 lies against the adjacent side of a heart valve.

Figure 6:
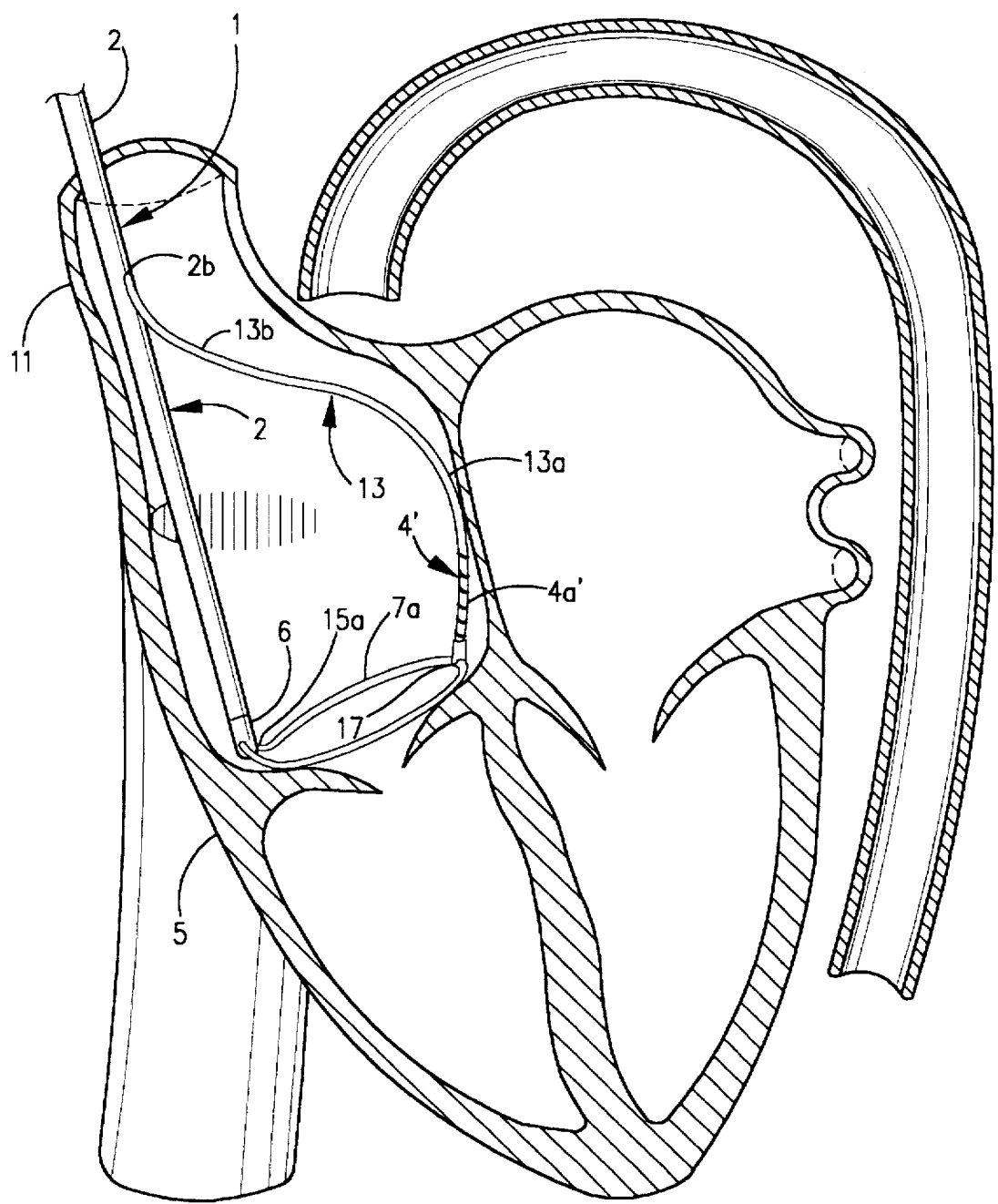
FIG. 6 is a view similar to that of FIG. 1 but showing a portion of a modified catheter which comprises two flexible guides.

The metallic or plastic wire which is used to make the guide 7 is resilient, i.e., it can reassume and tends to reassume a predetermined shape or orientation. Furthermore, the guide 7 includes a resiliently deformable section or portion 14 (FIG. 2) which causes the loop 7a to dwell in a predetermined plane until and unless the loop 7a is caused to move into a different plane, e.g., as a result of moving the loop against an internal surface in a body organ or due to the action of one or more additional guides such as a guide 13 which is shown in FIG. 6. The loop 7a of FIG. 4 is located in a plane which makes with the distal end 6 of the sheath a relatively large obtuse angle, e.g., an angle close to 135°.

Figure 5:
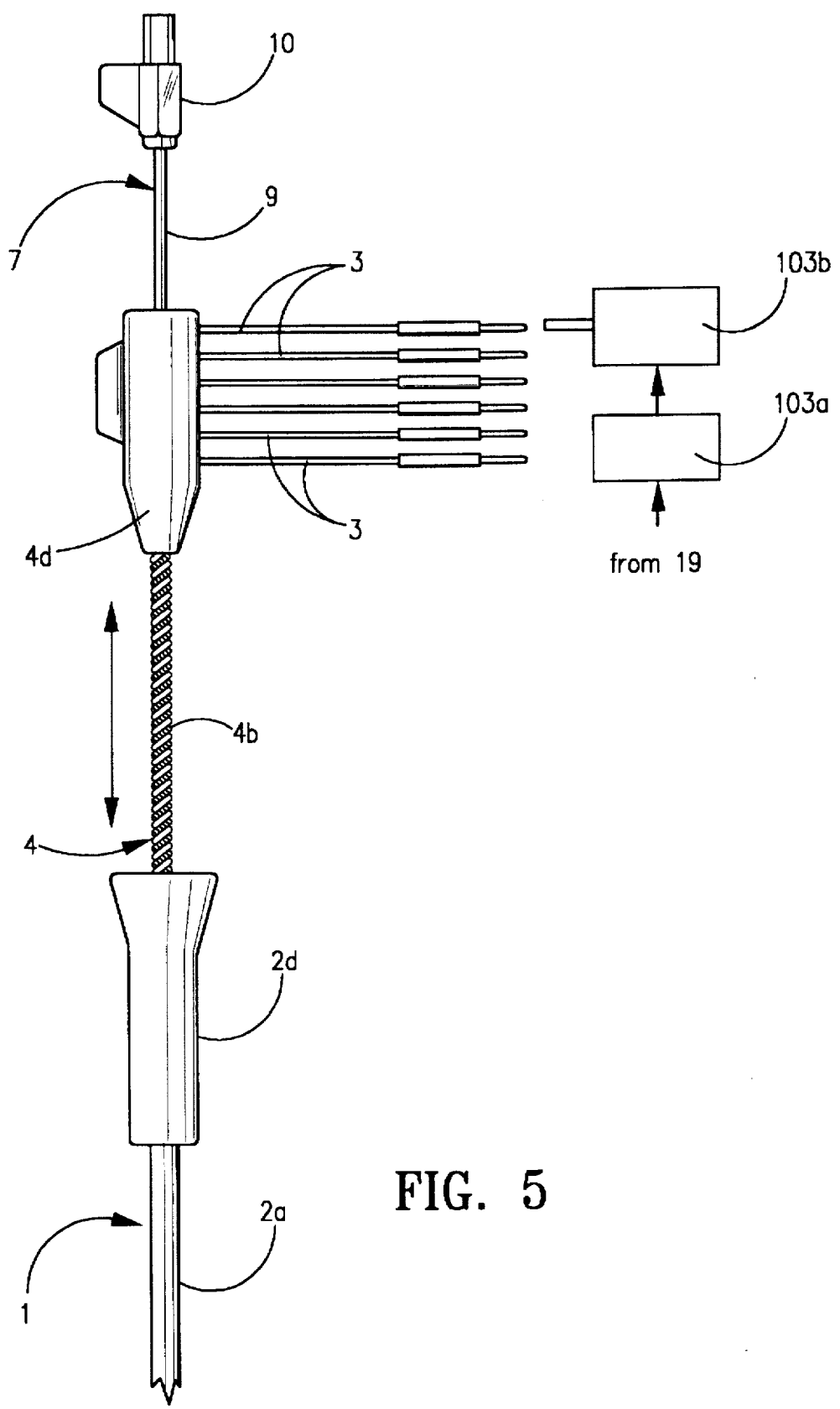
FIG. 5 is an enlarged partly elevational and partly diagrammatic view of the structure at the proximal end of the sheath forming part of the catheter shown in FIGS. 1 to 4.

The handgrip member 10 of FIG. 5 can be manipulated to move the strand 9 of the guide 7 between an infinite number of different positions relative to the sheath 2, i.e., the size of the loop 7a can be varied infinitely to thus ensure that the terminals of the conductors 3 can be moved to optimal positions relative to a selected internal surface of the heart 5 or another body organ.

The guide 7 of the catheter 1 shown in FIGS. 1 to 5 can be utilized as a means for steering the distal end portion 4a of the conductor assembly 4 to a predetermined position in a body organ and for maintaining the terminals of the conductors 3 in desired positions for the purposes of mapping, ablating or stimulating. However, the guide 7 can also serve as a means for steering to one or more desired positions the terminals of a conductor assembly (such as the conductor assembly 4 or a second conductor assembly 4' shown in FIG. 6). One of two conductor assemblies (such as 4 and 4') can be used to shift the distal end portion of the other conductor assembly relative to the loop 7a of the guide 7.

By retracting the handgrip portion 10 for the proximal end of the strand 9 to a position at a maximum distance from the handgrip portion 2d for the proximal end 2a of the sheath 2, the person in charge can reduce the size of the loop 7a to a minimum value. Thus, and if the distal end portion 4a of the conductor assembly 4 is withdrawn into the lumen 15 of the sheath 2 prior to a reduction of the size of the loop 7a to a minimum value, the still exposed portion of the wire or strand forming the guide 7 merely extends from the open end of the socket 16, along the rounded tip of the distal end 6 of the sheath 2, and into the outlet 15a of the lumen 15. This enables the person in charge to introduce the distal end or leader 6 of the sheath 2 into a selected blood vessel 11 and into a selected chamber of a heart 5 or another internal body organ. In other words, neither the guide 7 nor the conductor assembly 4 can interfere with rapid and trauma-free introduction of the distal end 6 of the sheath 2 into a selected portion of a body organ. However, once the distal end 6 has been advanced to a desired position, e.g., in a chamber of the heart 5, the person in charge can manipulate the handgrip portion 10 to increase the size of the loop 7a to any desired value in order to establish a path for advancement of the terminals 20 at the distal end portion 4a of the assembly 4 to desired positions in the selected chamber of the heart. FIG. 1 shows that the size of the loop 7a is selected with a view to ensure that the distal end portion 4a of the assembly 4 can be advanced along the loop 7a to any one of a practically infinite number of different positions relative to the adjacent side of the left-hand valve in the heart of FIG. 1. All that is necessary is to manipulate the handgrip portion 4d in order to move the distal end portion 4a of the assembly 4 along the loop 7a, either toward the socket 16 or in a direction from the socket 16 toward the outlet 15a of the lumen 15. The material of the loop 7a is sufficiently flexible to ensure that it can readily follow the outline of a selected internal surface of a body organ; this, in turn, ensures that the terminals 20 of the conductors 3 forming part of the assembly 4 can be moved sufficiently close to selected parts of the internal surface of an organ in order to guarantee satisfactory transmission of signals from such selected parts to one or more instruments which are connected to the proximal ends of the conductors 3 or to guarantee predictable transmission of stimuli or other signals to the selected parts of the internal surface.

As can be seen in FIG. 4, the loop 7a can form a circle which renders it possible to advance the terminals 20 of the conductors 3 along an arc of close to 360°. The handgrip portion 4d on the proximal end portion 4b of the assembly 4 can be moved relative to the handgrip portions 2d and 10 in stepwise fashion so that the distal end portion 4a of the assembly 4 can map or scan the selected portion of a surface in the heart 5 or another internal organ point-by-point. For example, the person in charge will advance the distal end portion 4a of the assembly 4 all the way to the end 8 of the loop 7a to thereupon retract the distal end portion 4a into the lumen 15 in stepwise fashion so that the terminals 20 can map a selected part of an internal surface of the heart 5 of FIG. 1 with a requisite degree of accuracy. At such time, the loop 7a ensures that the terminals 20 advance along a predetermined or preselected path. The mapping operation can be repeated as often as necessary, either along the previously mapped portion of the internal surface or along successively selected different portions of such internal surface.

The position of the loop 7a relative to the internal surface in the upper left-hand chamber of the heart 5 which is shown in FIG. 1 can be changed by merely shifting the distal end 6 of the sheath 2 by way of the handgrip portion 2d or subsequent to a reduction of the size of the loop 7a (with the handgrip portion 10) and, if necessary, subsequent to partial or complete retraction of the distal end portion 4a of the assembly 4 into the lumen 15.

The construction of the conductor assembly 4' which is shown in FIG. 6 is or can be identical with that of the assembly 4. Thus, the assemblies 4 and 4' can be used interchangeably to advance their distal end portions 4a, 4a' along the loop 7a or to advance their distal end portions 4a, 4a' along that portion of the guide 13 which extends from a second outlet 2b of the sheath 2. The outlet 2b is adjacent to but spaced apart from the outlet 15a so that a variable length of the strand 13b forming part of the guide 13 can extend between the distal end portion 4a' of the assembly 4' and the outlet 2b. The exposed portion of the strand 13b can be used as a means for propping the loop 7a against movement relative to a selected portion of the internal surface of the heart 5. The strand 13b (and more specifically that portion of the assembly 4' which surrounds the exposed length of the strand 13b) can engage the internal surface in the respective chamber of the heart 5 at a desired distance from the locus where a follower 17 (e.g., a hook or an eyelet) at the distal end 13a of the guide 13 slidably engages the loop 7a.

The helical convolutions of the conductor assembly 4 or 4' can constitute separately produced insulated wire-like components having proximal ends electrically connected to the conductors 3 shown in FIG. 5 and partially bare distal ends to form the terminals or poles 20. As already mentioned before, the diameter of the lumen 4c defined by the tube which forms part of the assembly 4 is sufficiently large to ensure that the wire-like material of the guide 7 can be slidably received therein. It is preferred to select the diameter of the lumen 4c in such a way that it can also slidably receive the wire of the guide 13. Analogously, the diameter of the lumen defined by the conductor assembly 4' is or can be selected in such a way that the lumen of the assembly 4' can slidably receive the wire of the guide 7 or the wire of the guide 13. This contributes to the versatility of the improved catheter. FIG. 4 shows, by way of example, that the diameter of the lumen 4c defined by the conductor assembly 4 exceeds the diameter of the wire which is used to make the guide 7.

The guide 13 may but need not always be provided with a section of the type shown at 14 in FIG. 2. The section 14 receives the desired shape in the manufacturing plant so that it continuously exhibits the tendency to maintain the loop 7a in a plane making a desired angle with the distal end 6 of the sheath. 2. The section 14 can be readily deformed in response to retraction of the loop 7a into the lumen 15 but is again ready to position the loop 7a in a predetermined plane (relative to the distal end 6) as soon as a portion of or the entire loop 7a shown in FIGS. 2 and 3 is expelled from the lumen 15 of the sheath 2. Once the leader or distal end 6 of the sheath is introduced into a selected chamber of the heart 5, adequate positioning of the loop 7a relative to the adjacent internal surface or surfaces of the heart does not necessitate any further shifting of the distal end 6, i.e., the person in charge manipulates the handgrip member 10 to select the size of the loop 7a and, once the loop properly engages the adjacent internal surface or surfaces, it performs the additional function of maintaining the distal end 6 in requisite position. The next step involves the manipulation of the handgrip portion 4d in order to move the terminals 20 of the distal end portion 4a to requisite positions relative to the adjacent internal surface or surfaces. As can be seen in FIG. 1, the provision of the arcuate section 14 ensures that the loop 7a can extend laterally of the distal end 6 and that the distal end 6 is located at one side of the left-hand valve in the heart 5.

The first end 8 of the loop 7a can be affixed to the distal end 6 of the sheath 2 in a manner other than that shown in FIG. 4. However, the placing of the socket 16 substantially diametrically opposite the outlet 15a of the lumen 15 is preferred at this time because this reduces the likelihood of excessive deformation of the wire forming the guide 7 when the size of the loop 7a is reduced to a minimum value.

The diameter of the lumen 15 in the sheath 2 is sufficiently large to ensure that the sheath can confine the strand 9 of the guide 7 as well as the strand 13b (FIG. 6) of the guide 13. However, it is equally within the purview of the invention to provide the sheath with two or more lumina, e.g., a discrete lumen for each of a plurality of guides (such as the guides 7, 13 and one or more additional guides, e.g., the guide 7' shown in FIG. 8).

The loop 7a of the guide 7 and the exposed distal end 13a of the guide 13 shown in FIG. 6 together constitute a three-dimensional guide assembly for a single conductor assembly 4 or 4' or for the conductor assemblies 4 and 4'. As can be seen in FIG. 6, the distal end portion 4a' of the assembly 4' can be moved along the exposed distal end portion 13a to ensure that the terminals of conductors forming part of the assembly 4' can be moved to requisite positions relative to the adjacent portion of the internal surface of the heart 5. The assembly 4 (not shown in FIG. 6 for the sake of clarity) can be used to shift the follower 17 at the tip of the distal end 13a of the guide 13 along the loop 7a, i.e., to establish different paths for movement of the distal end portion 4a' along the internal surface in the respective chamber of the heart 5. In lieu of the conductor assembly 4, the catheter of FIG. 6 can be furnished with a flexible hose or another tubular member (not shown) which can be slipped onto the guide 7 to move the follower 17 along the loop 7a of the guide 7. For example, the assembly 4 or 4' can be used to move its distal end portion 4a or 4a' along the distal end portion 13a of the guide 13 or along the loop 7a of the guide 7, and a discrete tubular moving device can be used to shift the follower 17 along the loop 7a.

An advantage of the three-dimensional framework including the guides 7 and 13 of FIG. 6 is that the loop 7a and/or the distal end portion 13a can be even more reliably held in a desired or optimum position prior to advancement of the distal end portion 4a or 4a' along the distal end portion 13a or along the loop 7a. Such reliable positioning of the distal end portion 13a and of the loop 7a further ensures that the assembly 4 and/or 4' can be used for accurate point-by-point mapping or scanning of the internal surface of a body organ.

The follower 17 of the distal end portion 13a of the guide 13 can constitute a hook, an eyelet or a relatively short sleeve having a passage which can receive the adjacent portion of and can be readily shifted along the loop 7a of the guide 7.

The improved catheter 1 can further serve as an ablation catheter. This can be achieved by providing the conductor assembly 4 and/or 4' with a terminal (note the terminal 18 in FIG. 4) which is connectable to a suitable source (103 in FIG. 5) of high-frequency energy. It is also possible to connect a plurality of conductors 3 of the assembly 4 or 4' with a source of high-frequency energy. The terminal or terminals 18 can be provided in addition to the terminal(s) 20 of the respective conductor(s) 3. FIG. 4 further shows a temperature sensor 19 which is carried by the distal end portion 4a of the conductor assembly 4 adjacent the terminal 18. It is also possible to install the temperature sensor 19 in the terminal 18. Signals from the temperature sensor 19 are or can be utilized to regulate the transmission of energy from the source 103 to the terminal 18. The temperature sensor 19 is connected to the regulating means 103a for the application of energy to the terminal 18 by one or more conductors in the lumen 4c of the distal end portion 4a of the conductor assembly 4.

The conductor assembly 4' can also comprise one or more terminals 18 connectable to the energy source 103 or to a separate source.

As already mentioned hereinbefore, the guide 7 and/or the guide or guides 13 and/or the guide 7' can be made of a metallic or plastic wire. It is presently preferred to employ a metallic wire, e.g., a wire made of NITINOL (Trademark). Such wire exhibits a highly satisfactory pronounced flexibility, pronounced resistance to buckling and the ability to repeatedly reassume a preselected shape even if its diameter is small or very small. Wire made of NITINOL can be obtained from NITINOL Development Corp., 48501 Warm Springs Blvd., Fremont, Calif. It is also possible to employ a wire made of TINEL (Trademark) which can be obtained from Raychem Corp., 300 Constitution Drive, Menlo Park, Calif.

Experiments indicate that a guide made of or containing NITINOL or TINEL can be caused to readily assume a desired shape, e.g., a loop 7a or 7a' (FIG. 8) made of such material can closely follow the outline of the surface bounding a chamber in the heart 5 in response to the application of relatively small forces to thus ensure atraumatic introduction into a body organ. However, once the application of force or forces to a loop made of NITINOL or TINEL is terminated, the loop automatically reassumes a preselected shape and moves into a plane making a selected angle with the distal end 6 of the sheath 2. A guide exhibiting the aforementioned desirable characteristics can be used to properly follow the outline of a surface in a heart and/or another body organ.

Figure 7:
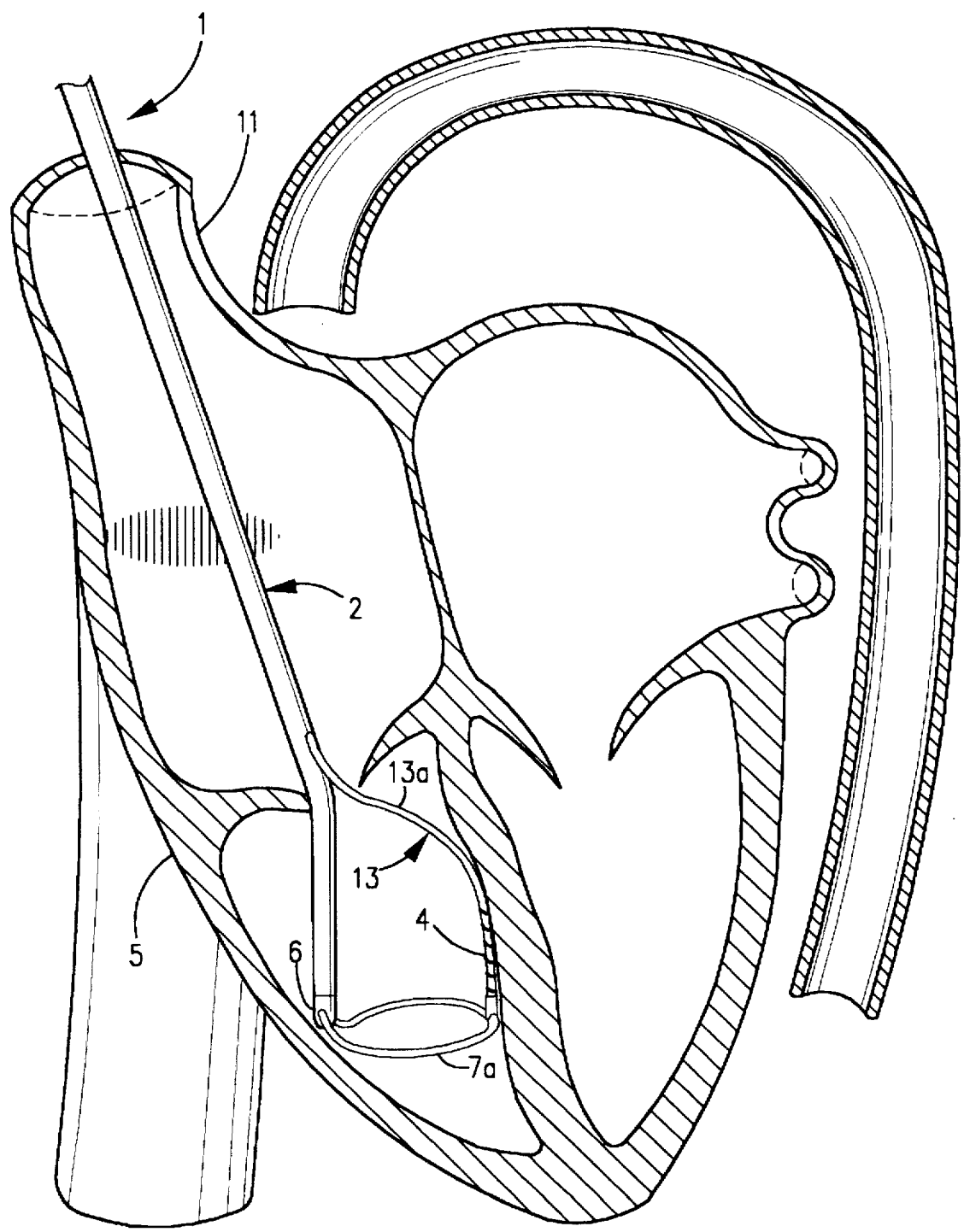
FIG. 7 is a view similar to that of FIG. 6 but showing the catheter with two flexible guides in another chamber of the heart.

The position of the loop 7a of the guide 7 which is shown in FIG. 1 is the same as that of the loop 7a shown in FIG. 6 but the loop 7a of FIG. 6 forms part of the aforementioned three-dimensional guide assembly because the catheter of FIG. 6 employs the guide 7 as well as the guide 13. FIG. 7 shows the catheter 1 of FIG. 6 but with the loop 7a and the distal end portion 13a of the guide 13 located in another internal chamber of the heart 5.

Figure 8:
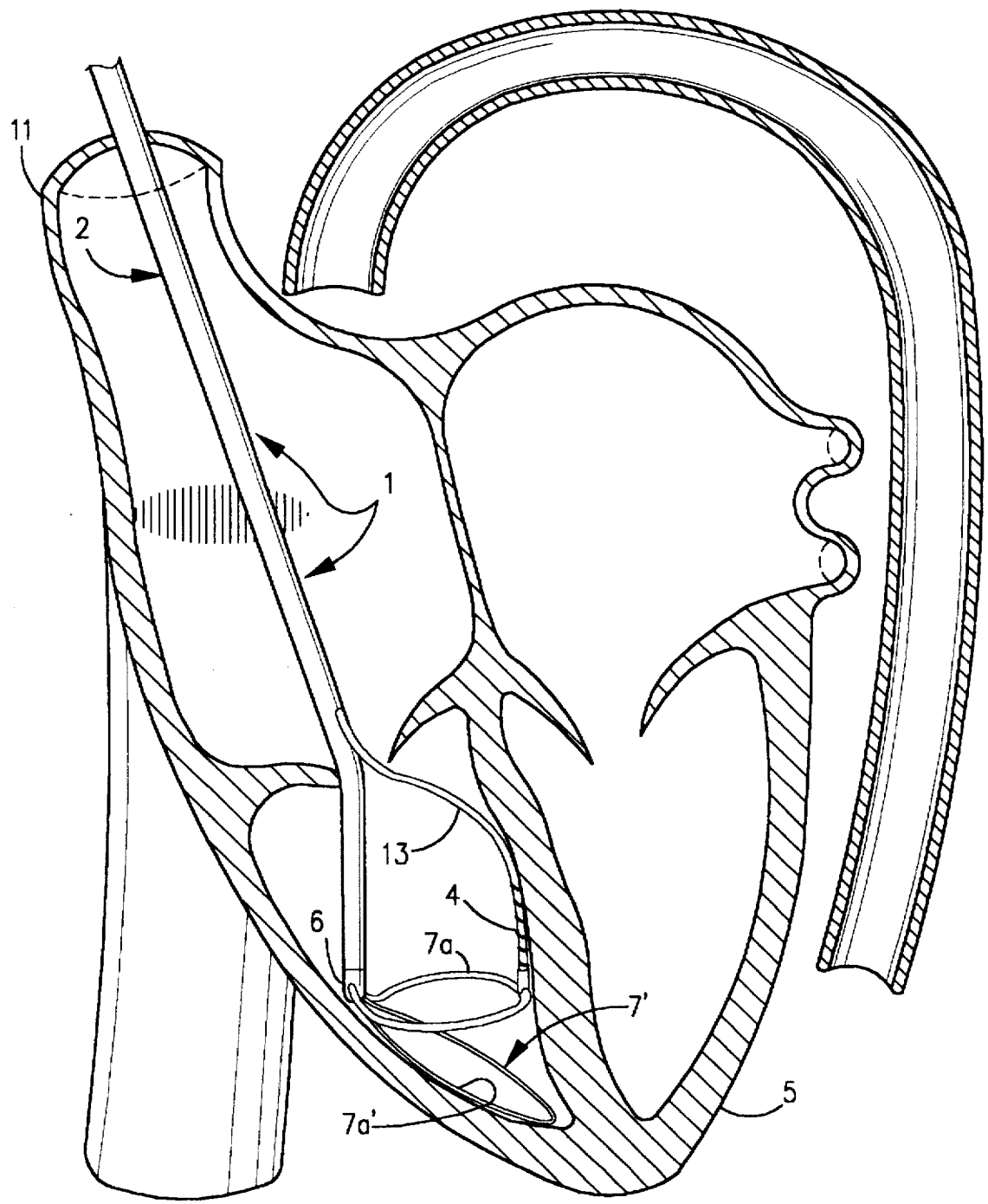
FIG. 8 is a view similar to that of FIG. 1, 6 or 7 but showing a portion of a third catheter which employs the flexible guides of FIG. 7 and a further flexible guide.

FIG. 8 illustrates the structure shown in FIG. 7 and the guide 7' which is or which can be identical with the guide 7 except that, in the absence of any stresses, its loop 7a' is located in a plane other than the plane of the loop 7a. The inclination of the plane for the loop 7a' relative to the distal end 6 of the sheath 2 is greater than that of the plane for the loop 7a. Thus, the follower of the distal end portion of the guide 13 is movable along the loop (7a) located in a plane making with the distal end 6 an angle which is smaller than the angle between the distal end 6 and the plane for the other loop (7a'). The catheter 1 of FIG. 1 can employ a first conductor assembly 4' which can be caused to move along the distal end portion of the guide 13, a second conductor assembly (corresponding to the assembly 4 shown in FIGS. 4, 5 and 7) and a third conductor assembly (not shown) which can be identical with or similar to the assembly 4 or 4' and can be caused to move its distal end portion along the loop 7a'. A single conductor assembly can be utilized to move its distal end portion along the distal end portion of the guide 13 or along the loop 7a or along the loop 7a'.

An important advantage of the catheter 1 which is shown in FIG. 8 is that the three-dimensional frame assembly including the guides 7, 7' and 13 renders it possible to even more reliably position the loop 7a, the loop 7a' and the distal end portion of the guide 13 relative to the adjacent portions of the surface bounding the respective chamber of the heart 5 or another internal body organ. Thus, the loop 7a extends along a first portion, the loop 7a' extends along a second portion, and the distal end portion of the guide 13 extends along a third portion of the surface bounding the cardiac chamber which receives the distal end 6 of the sheath 2. This renders it possible to carry out point-by-point mapping of the internal surface along the loop 7a and/or 7b and/or along the distal end portion of the guide 13 with an even higher degree of accuracy.

The catheter 1 of FIG. 8 can be utilized with particular advantage for mapping an internal surface close to the lowermost part of the heart 5. The frame assembly including the guides 7, 7' and 13 is sufficiently stable to establish preselected paths for the distal end portion of the conductor assembly 4 or 4' or an additional conductor assembly while being sufficiently flexible to ensure unimpeded pulsation of the heart. The strands of the guides 7, 7' and 13 can be confined in a common lumen (such as the lumen 15 shown in FIG. 4) or the sheath 2 of the catheter 1 shown in FIG. 8 can be provided with a plurality of lumina, e.g., one for each of the three strands.

FIG. 8 further shows that the second ends of the loops 7a and 7a' extend into a common outlet of the distal end 6 (such as the outlet 15a shown in FIG. 4) and that the first ends of such loops are anchored in the distal end 6 at a locus disposed at least substantially diametrically opposite the outlet. Though the distal end can be provided with a discrete outlet for each of the guides 7 and 7', the utilization of a single outlet (as shown in FIG. 8) is preferred because the two loops 7a and 7a' extend in the same direction (but in different planes) relative to the distal end 6. Such selection of the direction in which the loops 7a and 7a' extend from the distal end 6 has been found to contribute to more reliable positioning of the loops 7a and 7a' as well as of the distal end portion of the guide 13 in a selected chamber of the heart 5 or in a selected chamber (or a single chamber) of another body organ. The loops 7a, 7a' and the distal end portion of the guide 13 cooperate to maintain the distal end 6 of the sheath 2 in a selected position with reference to the wall bounding the respective internal chamber.

The catheter 1 of FIG. 8 can be simplified by omitting the guide 13, i.e., by utilizing only the two loops 7a and 7a' as a means for properly positioning the distal end of the catheter in an internal chamber or passage. However, the utilization of the guides 7 and 7' in combination with the guide 13 is preferred at this time because this enhances the versatility of the catheter by establishing a number of additional paths for the movement of the distal end portion of a conductor assembly along the distal end portion of the guide 13. The latter preferably includes a follower (not specifically shown in FIG. 8) which can resemble the follower 17 shown in FIG. 6 so that the distal end portion of the guide 13 can be shifted longitudinally of the loop 7a to establish a practically infinite number of paths for mapping in directions from the left-hand valve of the heart 5 shown in FIG. 8 toward the selected portion of the loop 7a.

Figure 9:
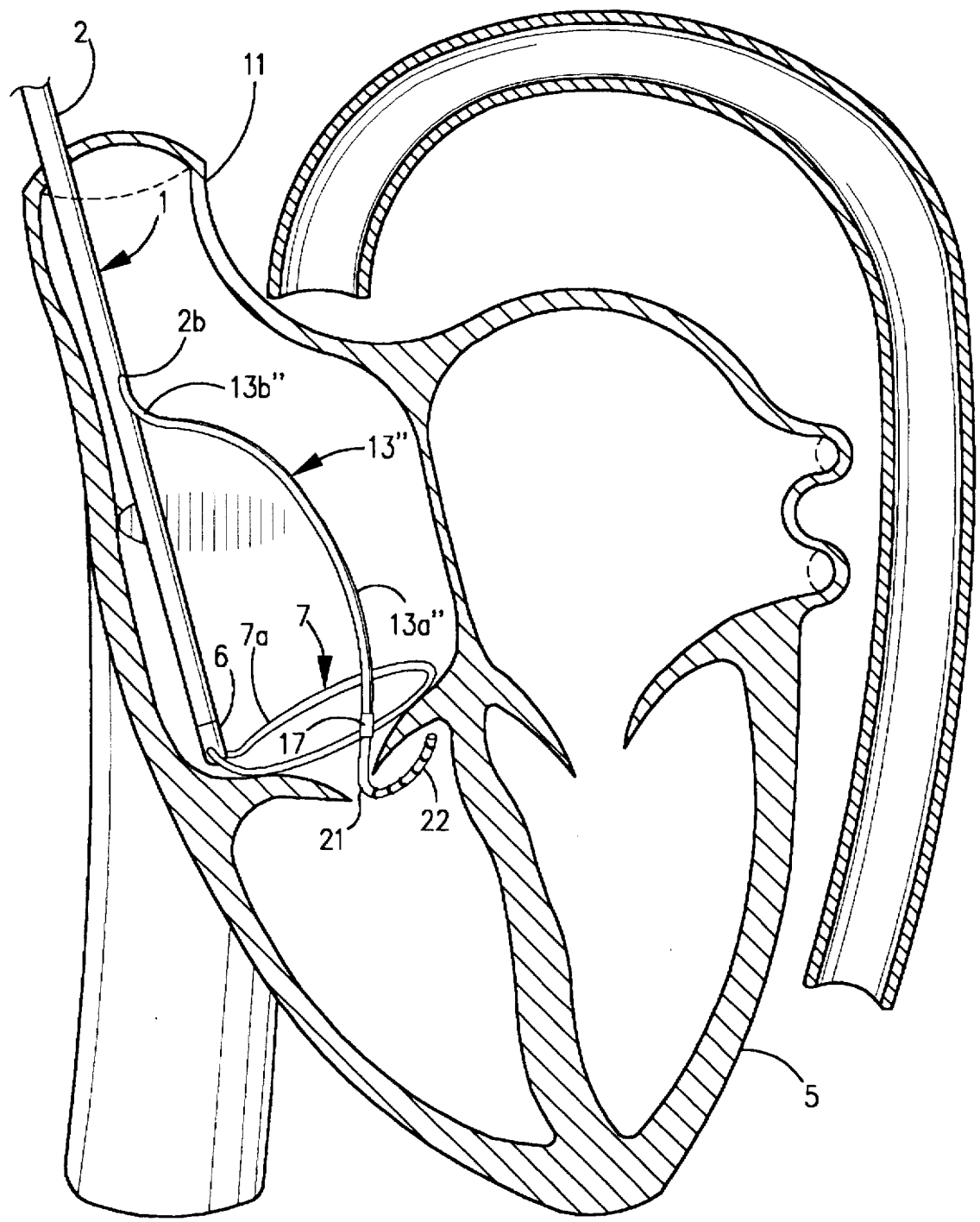
FIG. 9 is a view similar to that of FIG. 1, 6, 7 or 8 but showing a modified conductor assembly in the process of mapping one side of a heart valve.

FIG. 9 illustrates a further catheter 1 utilizing a first guide 7 having a loop 7a and a hollow tubular flexible guide 13" having a distal end portion 13a" provided with a follower 17 slidable along the loop 7a. The elongated median portion 13b" of the tubular guide 13" extends from the lumen of the sheath 2 through the outlet 2b and merges into the distal end portion 13a". The guide 13" has a lumen for a conductor assembly 21 which is slidable in such lumen and includes a substantially J-shaped distal end portion 22. The loop 7a is located at one side of the left-hand valve in the heart 5 of FIG. 9 and the distal end portion 22 of the assembly 21 extends through the opening in and toward the other side of such valve. Thus, the catheter 1 of FIG. 9 can be utilized for point-by-point mapping of one side of the valve by the distal end portion of a conductor assembly corresponding to the assembly 4 or 4', and for point-by point mapping of the other side of the valve by the terminals (not specifically shown) which are provided at the distal end portion 22 of the assembly 21. Furthermore, the J-shaped distal end portion 22 of the conductor assembly 21 cooperates with the adjacent portion of the heart valve to reduce the likelihood of undesirable shifting of the loop 7a relative to the respective side of the valve. A conductor assembly (such as 4 or 4') or a hose-like implement can be utilized to move the follower 17 of the tubular guide 13 along the loop 7a and to thus change the position of the distal end portion 22 of the assembly 21 relative to the underside of the left-hand valve in the heart 5 shown in FIG. 9.

The conductor assembly 21 of FIG. 9 can comprise one or more insulated conductors. The guide 13" can be said to constitute a second catheter which can be utilized in or with the catheter utilizing the sheath 2 and the guide 7 of FIG. 9. The follower 17 can be moved along the loop 7a by a conductor assembly 4 or 4' or by an implement resembling the tubular guide 13".

An important advantage of the catheter 1 which is shown in FIG. 9 is that it facilitates convenient, rapid and accurate mapping of that side of a heart valve (namely a side corresponding to the underside of the left-hand valve shown in FIG. 9) which cannot be readily mapped with heretofore known catheters. The conductor assembly 21 of FIG. 9 can be utilized for mapping or as an ablation instrument for surgical removal of tissue at the hard-to-reach side of a heart valve. If the assembly 21 is used as an ablation instrument, its distal end portion 22 is held in one or more selected positions by the loop 7a at the more readily accessible side of the valve. As mentioned above, a conductor assembly 4 or 4' (or a moving implement resembling the tubular guide 13") can be used to shift the follower 17 along the loop 7a to thereby advance the J-shaped distal end portion 22 of the assembly 21 to any of a practically infinite number of different positions.

FIGS. 10 and 11 illustrate the catheter 1 of FIG. 2 or 3, a conductor assembly 4 having a distal end portion movable along the loop 7a of the guide 7, and a conductor assembly 4' (which may be identical with the assembly 4) having a distal end portion movable along the guide 13. The distal end portion of the assembly 4 is movable along the loop 7a (in the directions indicated by a double-headed arrow Pf1) for the purpose of mapping, ablation, impulse transmission or impulse reception. In addition, the distal end portion of the assembly 4 is or can be used as a means for moving the follower 17 along the loop 7a. If the distal end portion of the assembly 4 is coupled to the follower 17, such distal end portion can move the follower in each of the two directions indicated by the double-headed arrow Pf1.

FIGS. 12 and 13 illustrate a portion of a catheter 1 which includes the sheath 2, the guide 7, and two guides 13 each having a follower 17 movable along the loop 7a of the guide 7. Each of the two followers 17 is movable in at least one of the two directions indicated by a double-headed arrow Pf2 by the distal end portion of a conductor assembly 4. The two followers 17 can be held at a selected distance from each other by a distancing element (e.g., a sleeve) which is slipped onto the loop 7a and is movable with the followers 17 in the directions indicated by the arrow Pf2. The distal end portion of each of the two guides 13 can guide the distal end portion of a discrete conductor assembly 4 so that the terminals of the assemblies 4 can map the adjacent portions of the internal surface of a body organ. The provision of a distancing element between the followers 17 of FIG. 13 further enhances the stability of the three-dimensional framework established by the loop 7a and the distal end portions of the two guides 13.

The catheter 1 of FIGS. 12 and 13 can be modified in a number of ways without departing from the spirit of the invention. For example, the three guides 7, 13, 13 which are shown in FIG. 13 can be used jointly with a further guide corresponding to the guide 7' of FIG. 8. The loop (7a') of such further guide can serve merely as a means for further stabilizing the framework established by the loop 7a and the distal end portions of the guides 13 and/or as a means for establishing an additional path for the movement of the distal end portion of a conductor assembly (e.g., an assembly 4) relative to the adjacent internal surface of a body organ.

It is also possible to modify the catheter 1 of FIGS. 12 and 13 in such a way that the modified catheter includes the guides 7 and 7' of FIG. 8 and the two guides 13 of FIG. 13. The distal end portion of one of the guides 13 can be provided with a follower which is slidable along the loop 7a of the guide 7, and the distal end portion of the other guide 13 can be provided with a follower slidable along the loop 7a' of the guide 7'.

The strands of the three guides 7, 13, 13 shown in FIG. 13 can be confined in a single lumen of the sheath 2 or each such strand can be confined in a discrete lumen.

An important advantage of the improved catheter is its versatility. Thus, the size of the single loop (7a or 7a') or the sizes of plural loops can be selected upon completed introduction of the distal end 6 of the sheath 2 into a heart or another organ. This ensures that the loop or loops closely follow the outline(s) of the adjacent portion(s) of the internal surface of the organ and establish optimal paths for the advancement of one or more conductor assemblies which are utilized to carry out a mapping, ablating, stimulating and/or other operation. By selecting the size(s) of the loop(s) upon introduction of the distal end 6 of the sheath into a body organ, the person in charge can ensure simple, convenient and rapid introduction of the distal end 6 to an optimum position for reliable anchoring of the loop or loops in a chamber by the simple expedient of thereafter increasing the size(s) of the loop(s) so that each loop remains in the selected position during advancement of the distal end portion of a conductor or conductor assembly therealong. By way of example, the distal end 6 can be introduced into the right auricle of a heart to ensure that the single loop or one of plural loops will adequately contact and will be reliably maintained in contact with the right ventricular valve during the following mapping, ablating, signal receiving or impulse transmitting operation.

If the improved catheter is to be used to carry out a mapping operation along one side of a cardiac valve (reference may be had to FIG. 1), the entire ring of such valve can be mapped by a conductor assembly 4 or 4' having, for example, six, eight or ten terminals or poles 20 at the respective distal end portion 4a or 4a'. The person in charge knows the number of terminals 20 and their mutual spacing along the distal end portion 4a or 4a', and such terminals are caused to advance along an arc of at least close to 360° in a direction from the first end of the loop (e.g., the first end 8 of the loop 7a) toward the outlet 15a of the lumen 15 or in the opposite direction. The terminals 20 transmit electric signals to a recording apparatus, not shown. Since the material (e.g., wire) of the guide 7 or 7' is readily flexible, the loop or loops do not interfere with pulsating movements of the heart but their material is sufficiently rigid to establish a predictable path for the advancement of the distal end portion 4a or 4a' of a conductor assembly 4 or 4' therealong. As already mentioned above, the wire which is used for the making of a guide 7, 7" or 13 can be made of a metallic material (such as NITINOL or TINEL) or of a suitable plastic (monofilamentary) material. All that counts is to ensure that the wire exhibits the aforementioned desirable characteristics regarding its flexibility, resiliency, memory and dimensions.

The catheters which are shown in FIGS. 6 to 13 exhibit the additional advantage that the provision of one or more additional guides (such as 13 and/or 13") even more reliably ensures that the selected path or paths for the distal end portion(s) of one or more conductor assemblies will remain unchanged in the course of a mapping or other operation. The loop 7a or 7a' or the loops 7a and 7a' then serve to properly position the distal end portion(s) of the guide(s) 13 and/or 13" or vice versa, depending upon whether the distal end portion of a conductor assembly is caused to advance along the loop 7a or 7a' or along the distal end portion(s) of the guide(s) 13 or within the distal end portion of the guide 13". For example, and referring again to FIG. 6, the size of the loop 7a can be selected in such a way that the loop maintains the distal end portion 13a of the guide 13 in an optimum position for advancement of the distal end portion 4a' of the conductor assembly 4' along a selected portion of the surface bounding the respective chamber of the heart 5. At the same time, the guide 13 maintains the loop 7a in an optimum position to guide the distal end portion of a conductor assembly (such as the distal end portion 4a of the assembly 4) along at least one half of the adjacent side of the valve at the distal end 6 of the sheath 2. Thus, the catheters which are shown in FIGS. 6 to 13 render it possible to dispense with regulatable electrodes and to complete a mapping or other operation within a fraction of the time required to complete the same operation with regulatable electrodes.

The feature that the size of a loop 7a or 7a' can be varied infinitely and that the length of the exposed distal end portion of a guide 13 or 13" is also variable at will further ensures that such size or sizes and/or length or lengths can be rapidly selected for the purpose of establishing one or more optimal paths for the advancement of the distal end portion or portions of one ore more conductor assemblies. The three-dimensional frameworks composed by the guides shown in FIGS. 6 to 13 are particularly suitable to ensure the establishment of optimal path or paths for the advancement of one or more conductor assemblies (i.e., one or more groups of terminals or poles) in the course of a mapping or other operation. This is due to the fact that the loop or loops of one or more guides 7, 7' reliably hold one or more guides 13 or 13" in selected positions and vice versa.

The diameters of the wires which are used to make the guides 7, 7' and 13 are preferably identical, and this preferably applies also for the diameters of lumens defined by the conductor assemblies 4 and 4'. This ensures that the assembly 4 or 4' can be caused to slide along the guide 7, 7' or 13.

The terminals or poles 20 can serve for point-by-point mapping of a selected portion or selected portions of a body organ to transmit appropriate signals (e.g., in the course of the mapping of an internal surface of a heart) and/or for determination of electrical potentials at various points of a heart.

Though it is also possible to select the length of a guide 7 or 7' in such a way that the loop 7a or 7a' constitutes a median portion of the guide and the guide further comprises two elongated strands (such as 9) each of which is slidable in the single lumen (15) or in one of several lumina in the sheath 2, the constructions which are shown in the drawings are preferred at this time because only one strand of each of the guides 7 and 7' must extend from the distal end 6 and all the way to the proximal end 2a of the sheath 2.

The provision of preformed section 14 as part of the guide 7 or 7' constitutes an optional but desirable and advantageous feature of the respective catheter. The section 14 ensures that the loop 7a or 7a' automatically assumes or tends to assume a desired position (in a plane which is inclined relative to the distal end 6 of the sheath 2) so that the loop 7a or 7a' can be rapidly and predictably located in an optimum position for the advancement of the distal end portion of a conductor assembly along a predetermined path. In the absence of the preformed section 14, the positioning of the loop 7a along the upper side of the left-hand heart valve shown in FIG. 6 would require extensive manipulation in order to flex the loop 7a from a plane which includes the axis of the distal end 6 into a plane which is shown in FIG. 6, namely at an oblique angle to the distal end 6. At the same time, the provision of the section 14 does not complicate the introduction of the distal end 6 of the sheath 2 into or its extraction from a chamber in a body organ because the wire of the guide 7 is sufficiently flexible to permit retraction of the entire loop 7a (or of a major portion of the loop 7a) into the lumen 15. However, when the loop 7a is even partially expelled from the lumen 15, the section immediately tends to move the loop into a plane which is inclined relative to the distal end 6 of the sheath 2.

Though it is possible to affix one end of a loop (such as the end 8 of the loop 7a shown in FIG. 4) to the external surface of the distal end 6 of the sheath 2, the provision of the socket 16 is preferred at this time because the end 8 of the loop 7a (i.e., of the wire of which the guide 7 is made) is less likely to interfere with the introduction of the distal end 6 into or with the extraction of such distal end from a chamber in the heart 5 or another organ. Furthermore, the end 8 of the loop 7a is less likely to become detached from the distal end 6 if it is anchored in the material of the sheath 2.

Each follower 17 could be fixedly secured to a selected portion of the loop 7a or 7a'. However, the provision of a follower which is slidable along the loop exhibits the important advantage that the entire loop can be retracted into the lumen 15 of the sheath 2. Referring again to FIG. 6, if the follower 17 is slidable along the loop 7a, the loop 7a can be practically completely retracted into the lumen 15 and the follower 17 is then located at the outlet 15a and only a very short or relatively short portion of the guide 13 remains exposed (namely that part of the distal end 13a which extends along a straight line between the outlets 2b and 15a of the sheath 2). Another advantage of a follower 17 which is slidable along the loop 7a or 7a' is that the distal end portion 13a of the guide 13 can be moved to an infinite number of positions in each of which the distal end portion 13a extends from the outlet 2b to a selected part of the loop 7a. In this way, a conductor assembly (such as the assembly 4' shown in FIG. 6) can map a circumferentially complete portion of the surface bounding the respective chamber in the heart 5 while the position of the loop 7a remains unchanged. All that is necessary is to shift the follower 17 along the loop 7a.

If the improved catheter is used as a means for transmitting to the heart 5 a series of stimulating impulses, such impulses can be transmitted by the conductor assembly 4 or 4' or by a tubular conductor comprising a single terminal or a number of conductors less than the number normally used to make a tube forming part of the conductor assembly 4 or 4'.

Regardless of whether a conductor assembly 4 or 4', or a flexible sleeve-like moving device, is used to shift the follower 17 along the loop 7a or 7a', such conductor assembly or such flexible sleeve also contributes to the stability of the three-dimensional framework which includes the guide 7 and/or 7' and one or more guides 13. Thus, the loop 7a or 7a' is even less likely to be displaced relative to the adjacent portion of the internal surface of a body organ if at least a part of such loop is surrounded by the means for shifting the follower to any one of a practically infinite number of different positions. If the follower is to be shifted by moving means other than the conductor assembly 4 or 4', such moving means can constitute an elongated flexible hose which can be slipped onto the guide 7 or 7' to move the follower along the loop 7a or 7a'. If the follower is to be shifted by the distal end portion of a conductor assembly (such as 4 or 4'), the conductor assembly can perform a plurality of different functions, namely moving the follower along the loop 7a or 7a', stiffening the three-dimensional framework including the guide 7 and/or 7' and one or more guides 13, and carrying out a mapping operation along the loop 7a or 7a'. The mapping operation along the distal end portion 13a of the guide 13 shown in FIG. 6 can precede or follow the mapping operation along the loop 7a or such mapping operations can be carried out simultaneously.

Ablation of unhealthy cells can immediately follow a mapping operation. Thus, the mapping operation can serve to determine the presence and location or locations of afflicted cells, and the following ablating operation is carried out to destroy the thus detected defective cells. All that is necessary is to connect at least one conductor 3 with the energy source 103 so that the corresponding terminal or pole 20 can be utilized to carry out the ablating operation. Though it is also possible to employ a discrete conductor or conductor assembly solely for the purposes of ablation, the utilization of one or more conductor assemblies (such as 4 and 4') having conductors connectable to the energy source 103 even further enhances the versatility of the improved catheter because the conductor assembly 4 and/or 4' can also serve to carry out a mapping operation. The energy source 103 can constitute a conventional high-frequency generator and the signals from the temperature sensor 19 are transmitted to the circuit 103A which regulates the operation of the generator 103 in a manner not forming part of the present invention. The circuit 103a prevents the temperature at the pole or terminal 18 from exceeding a predetermined maximum value. The predetermined temperature is selected in such a way that it suffices to carry out the ablating operation but is lower than that which could prove damaging to the neighboring (healthy) tissue.

Certain sections (corresponding to the section 14 shown in FIG. 2) of the plural loops 7a and 7a' can be selected in such a way that the loops 7a and 7a' exhibit the tendency to extend from the sockets in the distal end 6 to opposite sides of the sheath 2. It has been found that an orientation of the loops 7a and 7a' as shown in FIG. 8 exhibits a number of important advantages. Thus, these loops enable the distal end portion of a conductor assembly (such as 4 or 4') to carry out a number of mapping operations all the way around the respective portion of the internal chamber of the heart 5. Furthermore, the distal end portion of a conductor assembly which is caused to slide along the loop 7a or 7a' can be used to transmit to the heart 5 a series of stimulating impulses while the distal portion of the conductor assembly which is caused to slide along the loop 7a' or 7a can be used to carry out a mapping or ablating operation. It is also possible to provide the distal end 6 of the sheath 2 with a total of three outlets, namely an outlet 2b for the guide 13, an outlet 15a for the guide 7 and an outlet (e.g., adjacent the outlet 15a) for the guide 7'. The provision of two or more guides (such as 7 and 7') which are installed in such a way that they can be caused to develop loops at the distal end 6 of the sheath 2 exhibits the important advantage that it is even less likely to permit undesirable shifting of the path or paths for the distal end portion(s) of one or more conductor assemblies when the catheter is used to carry out a mapping, ablating or other operation in a heart, i.e., in an organ which performs pulsating movements during treatment or during mapping.

An advantage of a catheter which embodies the structure of FIGS. 12 and 13 is that it is even more likely to ensure that the paths for the advancement of the distal ends of conductor assemblies along the one and/or the other guide 13 and/or along the loop 7a remain unchanged in the course of a mapping or other operation while the organ (heart 5) performs a series of pulsating movements. The sheath 2, the plural guides 13 and the loop 7a together constitute a substantially basket-shaped framework which can yield so that it does not interfere with the pulsating movements of the heart but is sufficiently stable to continue to maintain the loop 7a and the distal end portions of the guides 13 in selected positions.

A catheter which embodies the structure of FIGS. 12 and 13 exhibits the additional advantage that it establishes a plurality of different paths for the advancement of the distal end portion(s) of one or more conductor assemblies along the internal surface of a body organ. The number of paths can be further increased by combining the features of the catheters of FIGS. 8 and 12-13, i.e., by employing a plurality of loops. Such plural loops can cooperate with the distal end portions of two or more guides 13 in order to further stabilize the three-dimensional framework and/or to establish one or more additional paths for the advancement of the distal ends of conductor assemblies.

The catheter of FIG. 9 is also susceptible of numerous additional modifications without departing from the spirit of the invention. For example, the tubular guide 13" can be used together with one or more (non-tubular) guides 13 to further stabilize the three-dimensional framework including the loop 7a and the guide 13" as well as to establish one or more additional paths for the distal end portions of conductor assemblies. As already mentioned before, the catheter of FIG. 9 exhibits the important advantage that the substantially J-shaped or hook-shaped distal end portion 22 of the conductor means 21 can be caused to map that side of the heart valve which faces away from the loop 7a, i.e., a side which cannot be mapped or treated with conventional catheters or which can be mapped or treated with conventional catheters only by entrusting the task to highly skilled practitioners and within an inordinately long interval of time.

It is further within the purview of the present invention to combine the features of the several illustrated and described catheters in a manner not specifically pointed out hereinbefore. All in all, in spite of its simplicity the improved catheter is more versatile than heretofore known catheters, it can be used to map and/or otherwise treat those parts of body organs which cannot be readily mapped and/or otherwise treated with heretofore known catheters, and the mapping and/or other operation(s) can be completed within surprisingly short intervals of time. The catheter can be readily introduced into a heart or into another body organ through a blood vessel or another body passage, and the introduction and/or extraction of the improved catheter is atraumatic because at least the major part of each guide can be completely or nearly completely retracted into the sheath 2. The properly inserted and enlarged loop 7a and/or 7a' can establish a reliable temporary force-locking or form-locking connection between the catheter and the body organ. Such connection between the improved catheter and a human or other animal heart does not affect the ability of the heart to carry out its pulsatory movements.

Another important advantage of the improved catheter is that it can be mass-produced at a reasonable cost. Thus, in its simplest form, the improved catheter will comprise the sheath 2, the guide 7 or 7', and the conductor assembly 4 or 4'. Moreover, the versatility of the improved catheter can be enhanced in a simple and inexpensive way, e.g., by employing two guides (such as 7 and 7') each of which can form a loop (7a or 7a'), by adding one or more guides 13 and/or by adding one or more guides 13".

Another metallic material which can be used to make the guide 7 and/or 7' and/or 13 is steel. The diameter of the metallic or plastic wire of which the guide 7 and/or 7' and/or 13 is made can be in the range between 0.3 and 0.5 mm.

If a pronounced versatility of a catheter which embodies the present invention is not important, the distal end portion of a conductor assembly (such as the end portion 4a of the assembly 4) can be affixed to the distal end 6 of the sheath 2, i.e., the conductor assembly need not be mounted for movement relative to the loop of the guide. The utilization of a catheter wherein the distal end portion of a conductor assembly is movable relative to the loop is preferred because the cross-sectional area of the distal end 6 can be reduced accordingly. Furthermore, the conductor assembly need not be as flexible as the guide 7, 7' or 13.

The sheath 2 can be provided with a row of two or more longitudinally spaced apart outlets for two or more guides 7 or 7' which are spaced apart from each other in the longitudinal direction of the sheath. Referring, for example, to the catheter of FIG. 8, the first and second ends of the loops 7a and 7a' can be spaced apart from each other in the longitudinal direction of the sheath, i.e., one or two loops can be spaced apart from the loop 7a or 7a' of FIG. 8 in a direction toward the proximal end of the sheath. This renders it possible to map and/or to ablate at two or more circumferentially complete portions of the surface bounding the chamber which receives the distal end 6 of the sheath 2 of FIG. 8. The spacing of two or more loops in the longitudinal direction of the sheath 2 can be such that the loop or loops 7a, 7a' assumes or assume the position(s) shown in FIG. 8 while a further loop engages the underside of the heart valve above the distal end 6 of the sheath 2 shown in FIG. 8. One or more loops can be provided between the further loop and the loops 7a, 7a' of FIG. 8.

Still further, it is possible to replace at least one of the conductor assemblies 4, 4' and 21 with an assembly composed of or comprising electrode pins and/or electrode rings. At least one of the guides can further serve as a means for facilitating the introduction of one or more inflatable balloons which serve as additional means for reliably maintaining the respective guide or guides in optimum positions for advancement of conductor assemblies along predetermined paths. For example, one or more balloons can be slipped onto or provided on the distal end portion 13a of the guide 13 shown in FIG. 6 to come into large-area contact with the adjacent portion of the internal surface of the heart 5. If the improved catheter employs or can be combined with one or more balloons, such catheter can further employ an endoscope including a bundle of optical fibers. After filling the balloon with a saline solution or with another suitable transparent medium, the person in charge can utilize the endoscope to inspect a wall or any other selected part of a heart. For example, the endoscope can be utilized to permit inspection for the purpose of ascertaining the presence or absence of the calcification of heart valves, to inspect the condition of lesions which develop as a result of ablation and/or for other purposes.

The catheter of FIG. 9 can be modified by selecting the dimensions of the lumen of the tubular guide 13" in such a way that it can confine two conductors or conductor assemblies 21 each having a substantially J-shaped distal end portion 22. This renders it possible to complete the mapping or ablation at the underside of the left-hand valve in the heart 5 of FIG. 9 within an even shorter interval of time. Furthermore, two or more substantially J-shaped distal end portions 22 are even more likely to maintain the loop 7a of FIG. 9 in a desired position during mapping or during ablation at the upper side of the valve which is located beneath the loop 7a of FIG. 9.

At least one of the conductor assemblies can be furnished with the aforediscussed temperature sensor 19, with one or more pressure sensors and/or with one or more pH sensors. The exact nature of the conductor assembly or assemblies will depend upon the electrophysiological tasks which are to be carried out by the catheter.

The conductor assembly (e.g., the conductor assembly 4 or 4') preferably constitutes a multicoil arrangement. The coil or coils are sufficiently stiff to push or pull the corresponding follower (such as the follower 17 shown in FIG. 11) in both directions along the respective guide. For example, the left-hand end of the conductor assembly shown in FIG. 11 can be affixed to the follower 17 so that the latter can be moved in the directions indicated by the arrow Pf1 in response to corresponding movements of the conductor assembly 4.

Figure 14:
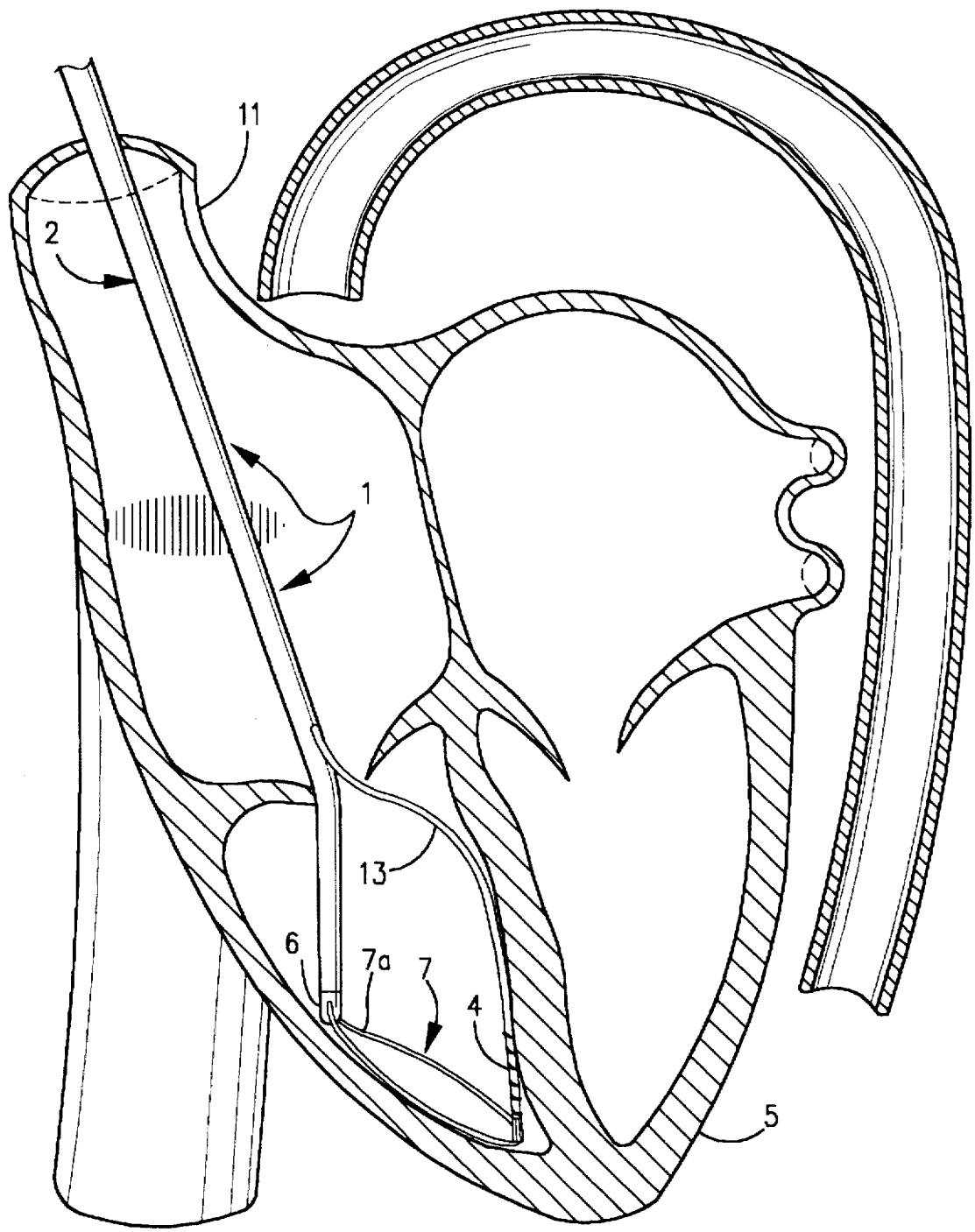
FIG. 14 is a view similar to that of FIG. 8 but with one of the guides omitted.

FIG. 14 shows the catheter of FIG. 8 but with the guide 7' and its loop 7a' omitted or withdrawn. The loop 7a of FIG. 14 occupies the same position as the loop 7a' of FIG. 8.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of the above outlined contribution to the art and, therefore, such adaptations should and are intended to be comprehended within the meaning and the range of equivalence of the appended claims.

What is claimed is:

1. A mapping and ablation catheter comprising an elongated flexible sheath having a distal end, a proximal end and at least one lumen between said ends; an elongated flexible guide having a looped portion at said distal end and a strand disposed in said at least one lumen and movable longitudinally of said sheath to thereby change the size of said looped portion; and conductor means having a distal end portion with at least one terminal and being movable longitudinally of and being guided by said strand to advance said distal end portion toward and along said looped portion.

2. The catheter of claim 1, wherein said conductor means comprises a plurality of discrete conductors each having a terminal at said distal end portion, said conductors forming part of a tube having a lumen for said flexible guide.

3. The catheter of claim 1, further comprising a second elongated flexible guide having a distal end portion movable along said looped portion and an elongated strand at least partially confined in and movable relative to said sheath to thereby move said looped portion relative to said distal end as well as to move the distal end portion of the second guide relative to and along said looped portion.

4. The catheter of claim 3, wherein said conductor means has a lumen which can receive either one of said strands preparatory to moving said distal end portion of said conductor means toward and away from the distal end portion of said second guide or toward and along said looped portion.

5. The catheter of claim 3, further comprising second conductor means having a distal end portion with at least one terminal, said second conductor means being movable longitudinally of the strand of said second guide to move the distal end portion of said second conductor means toward and away from the distal end portion of said second guide, said distal end portion of said second conductor means being movable along said looped portion jointly with the distal end portion of said second guide.

6. The catheter of claim 3, wherein said distal end portion of said second guide is movable between an infinite number of different positions relative to said distal end of said sheath as well as along said looped portion.

7. The catheter of claim 1, wherein said strand is movable relative to said sheath between an infinite number of different positions to thus infinitely vary the size of said looped portion.

8. The catheter of claim 1, wherein said conductor means comprises a plurality of discrete helically convoluted conductors which are insulated from each other and form part of a tube defining a lumen for said second guide, each of said conductors having an exposed terminal at the distal end portion of said conductor means.

9. The catheter of claim 8, wherein the lumen of said tube has a first diameter and said guide has a second diameter at most matching said first diameter so that said tube is readily slidable along the strand and the looped portion of said guide.

10. The catheter of claim 8, further comprising a second elongated flexible guide having a distal end portion movable along said looped portion and an elongated strand at least partially confined in and movable relative to said sheath, said second guide having a third diameter at most matching said first diameter so that said tube is readily slidable along the strand and the distal end portion of said second guide.

11. The catheter of claim 1, wherein said looped portion has a first end anchored in the distal end of said sheath and a second end merging into said strand, said strand having a proximal end at the proximal end of said sheath and said distal end portion of said conductor means being movable along and beyond the proximal end of said strand all the way toward and along said looped portion and all the way at least close to the first end of said looped portion.

12. The catheter of claim 1, wherein said looped portion has a first end affixed to said sheath at the distal end of the sheath and a second end merging into said strand, said guide including a resiliently deformable section disposed at and tending to maintain said looped portion in a plane making an obtuse angle with the distal end of said sheath.

13. The catheter of claim 12, wherein said resiliently deformable section of said guide is adjacent said first end of said looped portion.

14. The catheter of claim 1, wherein said at least one lumen has an outlet at the distal end of said sheath and said looped portion has a first end anchored in said distal end substantially diametrically opposite said outlet, said looped portion further having a second end merging into said strand and being movable by said strand relative to said sheath and said outlet to thus withdraw a selected part of the looped portion into said lumen or to increase that part of the looped portion which is located outside of the distal end of said sheath.

15. The catheter of claim 14, wherein the distal end of said sheath has a socket for the first end of said looped portion.

16. The catheter of claim 1, wherein said looped portion is disposed in a predetermined plane in the absence of deforming stresses upon the respective portion of said guide and further comprising a second guide having a distal end portion engaging said looped portion and an elongated strand confined in and movable longitudinally of said sheath, the distal end portion of said second guide being inclined with reference to said plane.

17. The catheter of claim 16, wherein the distal end portion of said second guide has a follower movable along said looped portion and said sheath has an outlet for the strand of said second guide, said outlet being spaced apart from the distal end of said sheath.

18. The catheter of claim 1, further comprising a second guide having a distal end portion disposed externally of the distal end of said sheath and a strand disposed in and movable longitudinally of said sheath, the distal end portion of said second guide having a follower slidably engaging said looped portion and further comprising means for moving said follower relative to said looped portion.

19. The catheter of claim 18, wherein said means for moving comprises the distal end portion of said conductor means.

20. The catheter of claim 18, wherein said means for moving includes a flexible tubular member having a lumen arranged to slidably receive the strand of said elongated flexible guide and a distal end portion movable along said looped portion to thereby move said follower relative to said looped portion.

21. The catheter of claim 18, wherein said means for moving includes second conductor means having a distal end portion movable along said looped portion to move said follower relative to said looped portion, said second conductor means including at least one discrete conductor having a terminal at the distal end portion of said second conductor means.

22. The catheter of claim 21, wherein said second conductor means includes a plurality of helically convoluted conductors together forming a tube with a lumen for said elongated flexible guide and each of said conductors having a terminal at the distal end portion of said second conductor means.

23. The catheter of claim 1, further comprising a second guide having a distal end portion outwardly adjacent the distal end of said sheath and an elongated strand disposed in and movable longitudinally of said sheath, and second elongated flexible conductor means including a distal end portion at the distal end portion of said second guide, said second conductor means including a tubular member defining a lumen having a first diameter and said second guide having a second diameter at most matching said first diameter, said second guide being received in said second conductor means and said second conductor means being movable longitudinally of said second guide to move the distal end portion of said second conductor means relative to the distal end portion of said second guide, said tubular member comprising at least one conductor having a terminal at the distal end portion of said second conductor means.

24. The catheter of claim 23, wherein said tubular member of said second conductor means comprises a plurality of helically convoluted conductors each having a terminal at the distal end portion of said second conductor means.

25. The catheter of claim 1, wherein said conductor means comprises at least one conductor having said at least one terminal and a proximal end disposed at the proximal end of said sheath and connectable to a source of high-frequency energy.

26. The catheter of claim 25, further comprising a temperature sensor at said at least one terminal.

27. The catheter of claim 26, further comprising means for regulating the transmission of high-frequency energy from said source to said at least one terminal in response to signals from said temperature sensor.

28. The catheter of claim 1, wherein said guide consists of elastically deformable material.

29. The catheter of claim 28, wherein the material of said guide is a metallic material.

30. The catheter of claim 28, wherein the material of said guide is a plastic material.

31. The catheter of claim 1, further comprising a second elongated flexible guide having a looped portion at said distal end and a strand disposed in and movable longitudinally of said sheath to vary the size of the respective looped portion, each of said looped portions being located in a different plane outwardly adjacent said distal end.

32. The catheter of claim 31, wherein the strands of said guides are confined in said at least one lumen and said at least one lumen has an outlet adjacent the looped portions of said guides.

33. The catheter of claim 31, wherein one of said planes makes with said distal end a first angle and the other of said planes makes with said distal end a larger second angle, and further comprising a third guide having a distal end portion engaging the looped portion in said one plane and a strand at least partially confined in and movable longitudinally of said sheath.

34. The catheter of claim 33, wherein the distal end portion of said third guide includes a follower movable along the looped portion in said one plane.

35. The catheter of claim 1, further comprising a plurality of additional guides each having a distal end portion engaging said looped portion and a strand at least partially confined in and movable longitudinally of said sheath.

36. The catheter of claim 35, wherein the distal end portion of at least one of said additional guides includes a follower movable along said looped portion.

37. The catheter of claim 1, further comprising a second guide including a looped portion externally adjacent said distal end and a strand at least partially confined in and movable longitudinally of said sheath to vary the size of the respective looped portion, and two additional guides each having a distal end portion engaging a different one of said looped portions and a strand at least partially confined in and movable longitudinally of said sheath.

38. The catheter of claim 1, further comprising a plurality of additional guides each having a distal end portion engaging said looped portion and a strand at least partially confined in and movable longitudinally of said sheath, the distal end portions of said additional guides being spaced apart from each other.

39. The catheter of claim 1, further comprising a hollow tubular second guide having a distal end portion at said looped portion and a second portion at least partially confined in said sheath, and second conductor means confined in said tubular guide and including a distal end portion movable beyond the distal end portion of said tubular guide.

40. The catheter of claim 39, wherein the distal end portion of said second conductor means is substantially J-shaped, said looped portion being movable against one side of a heart valve and said J-shaped distal end portion being movable through and toward the other side of such heart valve.

* * * * *